(12) United States Patent
Schneider et al.

(10) Patent No.: US 10,188,533 B2
(45) Date of Patent: *Jan. 29, 2019

(54) MINIMAL SURFACE AREA CONTACT DEVICE FOR HOLDING PLAQUE TO BLOOD VESSEL WALL

(75) Inventors: Peter Schneider, Honolulu, HI (US); Robert Giasolli, Honolulu, HI (US)

(73) Assignee: Intact Vascular, Inc., Wayne, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/790,819

(22) Filed: May 29, 2010

(65) Prior Publication Data

US 2011/0004237 A1 Jan. 6, 2011

Related U.S. Application Data

(63) Continuation-in-part of application No. 12/483,193, filed on Jun. 11, 2009, now Pat. No. 8,128,677.

(51) Int. Cl.
*A61F 2/848* (2013.01)
*A61F 2/88* (2006.01)
(Continued)

(52) U.S. Cl.
CPC ............... *A61F 2/86* (2013.01); *A61F 2/844* (2013.01); *A61F 2/848* (2013.01); *A61F 2/88* (2013.01);
(Continued)

(58) Field of Classification Search
CPC .............. A61F 2/848; A61F 2002/9155; A61F 2002/91558; A61F 2002/91566;
(Continued)

(56) References Cited

U.S. PATENT DOCUMENTS 3,221,746 A 12/1965 Noble
3,635,223 A 1/1972 Klieman
(Continued)

FOREIGN PATENT DOCUMENTS

AU 2008335140 11/2012
AU 2011274392 11/2013
(Continued)

OTHER PUBLICATIONS

Mosseri M, Rozenman Y, Mereuta A, Hasin Y, Gotsman M., "New Indicator for Stent Covering Area", in *Catheterization and Cardiovascular Diagnosis*, 1998, v. 44, pp. 188-192.
(Continued)

*Primary Examiner* — Tuan V Nguyen
(74) *Attorney, Agent, or Firm* — Knobbe Martens Olson & Bear, LLP

(57) ABSTRACT

A tack device for holding plaque against blood vessel walls in treating atherosclerotic occlusive disease is formed as a thin, annular band of durable, flexible material having a plurality of focal elevating elements on its outer annular periphery for holding loose plaque under a spring or other expansion force against a blood vessel wall. The focal elevating elements are designed to exert a holding force on a plaque position while minimizing the amount of material surface area in contact with the plaque or blood vessel wall and reducing the potential of friction with the intraluminal surface. This approach offers clinicians the ability to perform a minimally invasive post-angioplasty treatment and produce a stent-like result without using a stent.

17 Claims, 26 Drawing Sheets

(51) Int. Cl.
*A61F 2/86* (2013.01)
*A61F 2/844* (2013.01)
*A61F 2/91* (2013.01)
*A61F 2/92* (2013.01)
*A61F 2/95* (2013.01)
*A61F 2/82* (2013.01)

(52) U.S. Cl.
CPC . *A61F 2/91* (2013.01); *A61F 2/92* (2013.01); *A61F 2/95* (2013.01); *A61F 2002/823* (2013.01); *A61F 2002/825* (2013.01); *A61F 2002/826* (2013.01); *A61F 2002/8483* (2013.01); *A61F 2220/0016* (2013.01); *A61F 2230/005* (2013.01)

(58) Field of Classification Search
CPC .. A61F 2002/91575; A61F 2002/91508; A61F 2002/91525; A61F 2002/8483; A61F 2002/8486; A61F 2220/0008; A61F 2220/0016; A61F 2/02; A61F 2/04; A61F 2/06; A61F 2/07; A61F 2/82; A61F 2/86; A61F 2/89; A61F 2/915; A61F 2002/061; A61F 2002/068; A61F 2002/072; A61F 2002/075; A61F 2002/821; A61F 2002/823; A61F 2002/825; A61F 2002/826; A61F 2002/91516; A61F 2002/91533; A61F 2002/91541; A61F 2002/91583; A61F 2002/91591; A61F 2220/0025; A61F 2220/0091; A61B 2250/0029; A61B 2250/0037

See application file for complete search history.

(56) References Cited

U.S. PATENT DOCUMENTS

| | | | |
|---|---|---|---|
| 4,292,974 A | 10/1981 | Fogarty et al. | |
| 4,446,867 A | 5/1984 | Leveen et al. | |
| 4,465,072 A | 8/1984 | Tahari | |
| 4,515,587 A | 5/1985 | Schiff | |
| 4,545,367 A | 10/1985 | Tucci | |
| 4,545,390 A | 10/1985 | Leary | |
| 4,552,127 A | 11/1985 | Schiff | |
| 4,576,591 A * | 3/1986 | Kaye et al. | 604/62 |
| 4,589,412 A | 5/1986 | Kensey | |
| 4,641,654 A | 2/1987 | Samson et al. | |
| 4,651,738 A | 3/1987 | Demer et al. | |
| 4,687,465 A * | 8/1987 | Prindle et al. | 604/61 |
| 4,723,550 A | 2/1988 | Bales et al. | |
| 4,723,936 A | 2/1988 | Buchbinder et al. | |
| 4,723,938 A | 2/1988 | Goodin et al. | |
| 4,726,374 A | 2/1988 | Bales et al. | |
| 4,758,223 A | 7/1988 | Rydell | |
| 4,762,130 A | 8/1988 | Fogarty et al. | |
| 4,781,192 A | 11/1988 | Demer | |
| 4,784,636 A | 11/1988 | Rydell | |
| 4,846,174 A | 7/1989 | Willard et al. | |
| 4,848,342 A | 7/1989 | Kaltenbach | |
| RE33,166 E | 2/1990 | Samson | |
| 5,009,659 A | 4/1991 | Hamlin | |
| 5,024,668 A | 6/1991 | Peters et al. | |
| 5,042,707 A | 8/1991 | Taheri | |
| 5,047,015 A | 9/1991 | Foote et al. | |
| 5,102,390 A | 4/1992 | Crittenden et al. | |
| 5,196,024 A | 3/1993 | Barath | |
| 5,201,757 A | 4/1993 | Heyn et al. | |
| 5,242,452 A | 9/1993 | Inoue | |
| 5,246,420 A | 9/1993 | Kraus et al. | |
| 5,250,029 A | 10/1993 | Lin et al. | |
| 5,250,060 A | 10/1993 | Carbo et al. | |
| 5,263,962 A | 11/1993 | Johnson et al. | |
| 5,269,758 A | 12/1993 | Taheri | |
| 5,304,121 A | 4/1994 | Sahatjian | |
| 5,318,529 A | 6/1994 | Kontos | |
| 5,336,234 A | 8/1994 | Virgil | |
| 5,344,397 A | 9/1994 | Heaven et al. | |
| 5,383,890 A | 1/1995 | Miraki et al. | |
| 5,397,305 A | 3/1995 | Kawula et al. | |
| 5,397,355 A | 3/1995 | Marin et al. | |
| 5,421,955 A | 6/1995 | Lau et al. | |
| 5,423,851 A | 6/1995 | Samuels | |
| 5,423,885 A * | 6/1995 | Williams | A61F 2/92 606/194 |
| 5,501,689 A | 3/1996 | Green | |
| 5,534,007 A | 7/1996 | St. Germain et al. | |
| 5,536,252 A | 7/1996 | Imran et al. | |
| 5,540,659 A | 7/1996 | Teirstein | |
| 5,545,135 A | 8/1996 | Lacob et al. | |
| 5,562,728 A | 10/1996 | Lazarus et al. | |
| 5,569,272 A | 10/1996 | Reed | |
| 5,571,135 A | 11/1996 | Fraser et al. | |
| 5,591,197 A | 1/1997 | Orth et al. | |
| 5,593,417 A | 1/1997 | Rhodes | |
| 5,616,149 A | 4/1997 | Barath | |
| 5,634,928 A | 6/1997 | Fischell et al. | |
| 5,643,312 A | 7/1997 | Fischell et al. | |
| 5,665,116 A | 9/1997 | Chaisson | |
| 5,681,346 A | 10/1997 | Orth | |
| 5,704,913 A * | 1/1998 | Abele et al. | 604/101.02 |
| 5,725,572 A | 3/1998 | Lam et al. | |
| 5,728,158 A | 3/1998 | Lau et al. | |
| 5,743,874 A | 4/1998 | Fischell et al. | |
| 5,746,716 A * | 5/1998 | Vigil et al. | 604/97.01 |
| 5,746,764 A | 5/1998 | Green et al. | |
| 5,776,161 A | 7/1998 | Globerman | |
| 5,797,951 A | 8/1998 | Mueller | |
| 5,800,526 A * | 9/1998 | Anderson et al. | 623/1.16 |
| 5,813,977 A | 9/1998 | Hinchliffe et al. | |
| 5,817,152 A | 10/1998 | Birdsall et al. | |
| 5,833,694 A * | 11/1998 | Poncet | 623/1.11 |
| 5,843,033 A * | 12/1998 | Ropiak | 604/103.01 |
| 5,911,725 A | 6/1999 | Boury | |
| 5,925,061 A | 7/1999 | Ogi et al. | |
| 5,928,247 A * | 7/1999 | Barry et al. | 264/171.12 |
| 5,954,742 A * | 9/1999 | Osypka | 606/198 |
| 5,957,949 A | 9/1999 | Leonhardt et al. | |
| 5,968,068 A | 10/1999 | Dehdashtian et al. | |
| 5,968,088 A | 10/1999 | Hansen et al. | |
| 5,972,023 A | 10/1999 | Tanner et al. | |
| 5,980,552 A | 11/1999 | Pinchasik et al. | |
| 6,004,328 A | 12/1999 | Solar | |
| 6,007,543 A | 12/1999 | Ellis | |
| 6,009,614 A | 1/2000 | Morales | |
| 6,013,854 A | 1/2000 | Moriuchi | |
| 6,036,725 A * | 3/2000 | Avellanet | 623/1.13 |
| 6,048,360 A * | 4/2000 | Khosravi et al. | 623/1.11 |
| 6,053,941 A | 4/2000 | Lindenberg et al. | |
| 6,053,943 A | 4/2000 | Edwin | |
| 6,080,177 A | 6/2000 | Igaki | |
| 6,090,135 A | 7/2000 | Plaia et al. | |
| 6,110,198 A | 8/2000 | Fogarty et al. | |
| 6,123,722 A * | 9/2000 | Fogarty et al. | 623/1.1 |
| 6,126,685 A * | 10/2000 | Lenker et al. | 623/1.11 |
| 6,129,754 A | 10/2000 | Kanesaka et al. | |
| 6,139,573 A * | 10/2000 | Sogard et al. | 623/1.13 |
| 6,143,016 A | 11/2000 | Bleam et al. | |
| 6,146,358 A | 11/2000 | Rowe | |
| 6,152,937 A * | 11/2000 | Peterson et al. | 606/153 |
| 6,157,852 A | 12/2000 | Selmon et al. | |
| 6,165,199 A | 12/2000 | Barbut | |
| 6,187,034 B1 | 2/2001 | Frantzen | |
| 6,197,013 B1 | 3/2001 | Reed | |
| 6,197,103 B1 | 3/2001 | Reed | |
| 6,200,336 B1 | 3/2001 | Pavcnik et al. | |
| 6,203,568 B1 | 3/2001 | Lombardi et al. | |
| 6,203,569 B1 * | 3/2001 | Wijay | 623/1.15 |
| 6,221,102 B1 | 4/2001 | Baker | |
| 6,241,667 B1 | 6/2001 | Vetter et al. | |
| 6,254,628 B1 * | 7/2001 | Wallace et al. | 623/1.12 |
| 6,258,117 B1 * | 7/2001 | Camrud et al. | 623/1.16 |
| 6,266,550 B1 | 7/2001 | Selmon et al. | |
| 6,270,524 B1 | 8/2001 | Kim | |

(56) References Cited

U.S. PATENT DOCUMENTS

| | | |
|---|---|---|
| 6,273,909 B1 | 8/2001 | Kugler et al. |
| 6,290,728 B1 * | 9/2001 | Phelps et al. ............... 623/23.7 |
| 6,312,444 B1 | 11/2001 | Barbut |
| 6,312,460 B2 | 11/2001 | Drasler et al. |
| 6,325,824 B2 | 12/2001 | Limon |
| 6,344,053 B1 | 2/2002 | Boneau |
| 6,364,901 B1 | 4/2002 | Inoue |
| 6,364,904 B1 * | 4/2002 | Smith ........................ 623/1.22 |
| 6,371,962 B1 | 4/2002 | Ellis |
| 6,387,113 B1 * | 5/2002 | Hawkins et al. ............. 606/219 |
| 6,402,777 B1 | 6/2002 | Globerman |
| 6,409,863 B1 | 6/2002 | Williams et al. |
| 6,425,915 B1 * | 7/2002 | Khosravi et al. ............ 623/1.22 |
| 6,428,550 B1 | 8/2002 | Vargas et al. |
| 6,428,566 B1 | 8/2002 | Holt |
| 6,475,237 B2 * | 11/2002 | Drasler et al. ............... 623/1.15 |
| 6,485,510 B1 | 11/2002 | Camrud et al. |
| 6,491,707 B2 | 12/2002 | Makower et al. |
| 6,508,822 B1 * | 1/2003 | Peterson et al. ............. 606/153 |
| 6,517,573 B1 | 2/2003 | Pollock et al. |
| 6,527,800 B1 | 3/2003 | McGuckin, Jr. et al. |
| 6,547,817 B1 | 4/2003 | Fischell et al. |
| 6,551,353 B1 * | 4/2003 | Baker et al. ................. 623/1.42 |
| 6,648,911 B1 * | 11/2003 | Sirhan et al. ................ 623/1.15 |
| 6,660,031 B2 | 12/2003 | Tran et al. |
| 6,692,504 B2 | 2/2004 | Kurz |
| 6,699,277 B1 | 3/2004 | Freidberg et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,730,116 B1 | 5/2004 | Wolinsky et al. |
| 6,746,475 B1 * | 6/2004 | Rivelli, Jr. ................. 623/1.15 |
| 6,752,828 B2 * | 6/2004 | Thornton ................... 623/1.24 |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 * | 11/2004 | Chuter ........................ 623/1.35 |
| 6,827,731 B2 * | 12/2004 | Armstrong et al. .......... 623/1.12 |
| 6,843,400 B1 * | 1/2005 | Lee ................................. 227/8 |
| 6,849,087 B1 | 2/2005 | Chuter |
| 6,896,697 B1 * | 5/2005 | Yip ........................ A61F 2/915 623/1.15 |
| 6,899,718 B2 | 5/2005 | Gifford, III et al. |
| 6,913,600 B2 | 7/2005 | Valley et al. |
| 6,942,680 B2 | 9/2005 | Grayz |
| 6,951,554 B2 | 10/2005 | Johansen et al. |
| 6,986,784 B1 * | 1/2006 | Weiser et al. ................. 623/1.1 |
| 7,001,422 B2 | 2/2006 | Escamilla et al. |
| 7,001,424 B2 * | 2/2006 | Patel et al. ................... 623/1.15 |
| 7,007,698 B2 * | 3/2006 | Thornton ...................... 128/898 |
| 7,018,402 B2 * | 3/2006 | Vito et al. .................... 623/1.15 |
| 7,025,791 B2 * | 4/2006 | Levine et al. ............. 623/23.64 |
| 7,037,330 B1 * | 5/2006 | Rivelli, Jr. ............... A61F 2/91 623/1.11 |
| 7,041,130 B2 * | 5/2006 | Santini et al. ............... 623/1.42 |
| 7,087,088 B2 * | 8/2006 | Berg et al. ................. 623/23.64 |
| 7,122,043 B2 * | 10/2006 | Greenhalgh et al. ......... 606/191 |
| 7,137,993 B2 | 11/2006 | Acosta et al. |
| 7,147,655 B2 | 12/2006 | Chermoni |
| 7,147,656 B2 * | 12/2006 | Andreas et al. ............. 623/1.11 |
| 7,147,661 B2 | 12/2006 | Chobotov et al. |
| 7,150,745 B2 * | 12/2006 | Stern et al. ...................... 606/41 |
| 7,160,312 B2 * | 1/2007 | Saadat ........................ 606/153 |
| 7,163,552 B2 * | 1/2007 | Diaz ........................... 623/1.12 |
| 7,166,125 B1 | 1/2007 | Baker et al. |
| 7,169,158 B2 | 1/2007 | Sniffin et al. |
| 7,169,163 B2 | 1/2007 | Becker |
| 7,179,284 B2 | 2/2007 | Khosravi |
| 7,192,440 B2 | 3/2007 | Andreas et al. |
| 7,201,770 B2 * | 4/2007 | Johnson et al. ............. 623/1.12 |
| 7,211,101 B2 * | 5/2007 | Carley et al. ................ 606/213 |
| 7,258,697 B1 * | 8/2007 | Cox .......................... A61F 2/91 623/1.14 |
| 7,261,731 B2 * | 8/2007 | Patel et al. ................... 623/1.15 |
| 7,267,684 B2 | 9/2007 | Rolando et al. |
| 7,270,673 B2 | 9/2007 | Yee |
| 7,273,492 B2 | 9/2007 | Cheng et al. |
| 7,279,007 B2 | 10/2007 | Nikolic et al. |
| 7,294,146 B2 * | 11/2007 | Chew et al. ................. 623/1.12 |
| 7,296,577 B2 | 11/2007 | Lashinski et al. |
| 7,300,456 B2 | 11/2007 | Andreas et al. |
| 7,303,572 B2 | 12/2007 | Meisheimer |
| 7,306,617 B2 | 12/2007 | Majercak |
| 7,309,341 B2 | 12/2007 | Ortiz et al. |
| 7,309,350 B2 | 12/2007 | Landreville et al. |
| 7,323,006 B2 | 1/2008 | Andreas et al. |
| 7,323,007 B2 | 1/2008 | Sano |
| 7,326,236 B2 | 2/2008 | Andreas et al. |
| 7,329,279 B2 * | 2/2008 | Haug et al. .................. 623/2.11 |
| 7,331,987 B1 | 2/2008 | Cox |
| 7,331,992 B2 * | 2/2008 | Randall et al. .............. 623/1.36 |
| 7,351,255 B2 | 4/2008 | Andreas |
| 7,399,307 B2 | 7/2008 | Evans et al. |
| 7,402,168 B2 * | 7/2008 | Sanderson et al. .......... 623/1.11 |
| 7,431,729 B2 * | 10/2008 | Chanduszko ................ 606/213 |
| 7,445,631 B2 * | 11/2008 | Salahieh et al. ............. 623/2.18 |
| 7,476,245 B2 | 1/2009 | Abbate |
| 7,500,986 B2 | 3/2009 | Lye et al. |
| 7,510,575 B2 * | 3/2009 | Spenser et al. .............. 623/2.18 |
| 7,524,330 B2 | 4/2009 | Berreklouw |
| 7,537,607 B2 | 5/2009 | Gerberding |
| 7,604,662 B2 | 10/2009 | Cambronne et al. |
| 7,617,007 B2 * | 11/2009 | Williams et al. ............. 607/126 |
| 7,618,432 B2 * | 11/2009 | Pedersen et al. ............ 606/194 |
| 7,618,447 B2 | 11/2009 | Case et al. |
| 7,628,803 B2 | 12/2009 | Pavcnik et al. |
| 7,655,034 B2 | 2/2010 | Mitchell et al. |
| 7,666,216 B2 | 2/2010 | Hogendijk et al. |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,594 B2 | 7/2010 | Lamson et al. |
| 7,758,627 B2 | 7/2010 | Richter |
| 7,758,632 B2 * | 7/2010 | Hojeibane et al. ........... 623/1.24 |
| 7,763,063 B2 | 7/2010 | Arbefeuille et al. |
| 7,806,918 B2 | 10/2010 | Nissl et al. |
| 7,833,262 B2 | 11/2010 | McGuckin, Jr. et al. |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,922,755 B2 | 4/2011 | Acosta et al. |
| 7,933,660 B2 | 4/2011 | Carr |
| 7,955,315 B2 | 6/2011 | Feinberg et al. |
| 7,963,987 B2 | 6/2011 | Melsheimer et al. |
| 7,967,855 B2 | 6/2011 | Furst et al. |
| 7,972,373 B2 | 7/2011 | Contiliano et al. |
| 8,002,725 B2 | 8/2011 | Hogendijk |
| 8,024,851 B2 * | 9/2011 | Barr et al. ....................... 29/557 |
| 8,034,099 B2 | 10/2011 | Pellegrini |
| 8,043,354 B2 | 10/2011 | Greenberg et al. |
| 8,048,151 B2 | 11/2011 | O'Brien et al. |
| 8,052,738 B2 | 11/2011 | Craven |
| 8,128,677 B2 | 3/2012 | Schneider et al. |
| 8,157,851 B2 | 4/2012 | Andreas |
| 8,177,831 B2 | 5/2012 | Andreas |
| 8,236,045 B2 | 8/2012 | Benichou et al. |
| 8,292,938 B2 | 10/2012 | Case |
| 8,308,790 B2 | 11/2012 | Arbefeuille et al. |
| 8,317,859 B2 | 11/2012 | Snow et al. |
| 8,323,243 B2 | 12/2012 | Schneider et al. |
| 8,353,945 B2 | 1/2013 | Andreas et al. |
| 8,366,766 B2 | 2/2013 | Berreklouw |
| 8,394,139 B2 | 3/2013 | Roeder et al. |
| 8,403,978 B2 | 3/2013 | Schlun et al. |
| 8,414,636 B2 | 4/2013 | Nabulsi et al. |
| 8,460,357 B2 | 6/2013 | McGarry et al. |
| 8,474,460 B2 | 7/2013 | Barrett et al. |
| 8,500,787 B2 | 8/2013 | Simpson et al. |
| 8,500,789 B2 | 8/2013 | Wuebbeling et al. |
| 8,540,760 B2 | 9/2013 | Paul, Jr. et al. |

(56) References Cited

U.S. PATENT DOCUMENTS

| | | | |
|---|---|---|---|
| 8,585,747 B2 | 11/2013 | Andreas et al. | |
| 8,784,467 B2 | 7/2014 | Connelly et al. | |
| 8,864,811 B2 | 10/2014 | Kao | |
| 8,888,841 B2 | 11/2014 | Pandelidis et al. | |
| 8,900,289 B2 | 12/2014 | Thompson | |
| 8,956,398 B2 | 2/2015 | George et al. | |
| 8,986,362 B2 | 3/2015 | Snow et al. | |
| 9,050,181 B2 | 6/2015 | Hartley | |
| 9,113,999 B2 | 8/2015 | Taylor et al. | |
| 9,216,082 B2 | 12/2015 | Von Segesser et al. | |
| 9,237,959 B2 | 1/2016 | Cage | |
| 9,301,864 B2 | 4/2016 | Kao | |
| 9,370,437 B2 | 6/2016 | Chuter et al. | |
| 9,398,967 B2 | 7/2016 | Cornelius | |
| 9,918,835 B2 | 3/2018 | Guyenot et al. | |
| 2002/0007211 A1 | 1/2002 | Pinchasik et al. | |
| 2002/0052641 A1* | 5/2002 | Monroe et al. | 623/1.11 |
| 2002/0055772 A1 | 5/2002 | McGuckin, Jr. et al. | |
| 2002/0120323 A1 | 8/2002 | Thompson | |
| 2002/0123790 A1 | 9/2002 | White et al. | |
| 2002/0143386 A1 | 10/2002 | Davila et al. | |
| 2002/0169495 A1* | 11/2002 | Gifford et al. | 623/1.11 |
| 2003/0018377 A1 | 1/2003 | Berg et al. | |
| 2003/0055491 A1 | 3/2003 | Schwartz et al. | |
| 2003/0069630 A1 | 4/2003 | Burgermeister et al. | |
| 2003/0130720 A1 | 7/2003 | DePalma et al. | |
| 2003/0158595 A1* | 8/2003 | Randall et al. | 623/1.13 |
| 2003/0191479 A1 | 10/2003 | Thornton | |
| 2003/0220683 A1 | 11/2003 | Minasian et al. | |
| 2003/0225446 A1 | 12/2003 | Hartley | |
| 2003/0225448 A1 | 12/2003 | Gerberding | |
| 2004/0010307 A1* | 1/2004 | Grad et al. | 623/1.15 |
| 2004/0039414 A1* | 2/2004 | Carley et al. | 606/213 |
| 2004/0098077 A1 | 5/2004 | Gianotti | |
| 2004/0098098 A1* | 5/2004 | McGuckin et al. | 623/1.14 |
| 2004/0106977 A1* | 6/2004 | Sullivan et al. | 623/1.12 |
| 2004/0143287 A1 | 7/2004 | Konstantino | |
| 2004/0186551 A1* | 9/2004 | Kao et al. | 623/1.15 |
| 2004/0215324 A1 | 10/2004 | Vonderwalde et al. | |
| 2004/0215326 A1 | 10/2004 | Goodson, IV et al. | |
| 2004/0215331 A1* | 10/2004 | Chew | A61F 2/91 623/1.21 |
| 2004/0230293 A1 | 11/2004 | Yip | |
| 2004/0260391 A1* | 12/2004 | Santini et al. | 623/1.42 |
| 2004/0267348 A1* | 12/2004 | Gunderson et al. | 623/1.12 |
| 2005/0010275 A1 | 1/2005 | 'Sahatjian | |
| 2005/0070921 A1* | 3/2005 | Ortiz et al. | 606/139 |
| 2005/0096727 A1 | 5/2005 | Allen et al. | |
| 2005/0096731 A1* | 5/2005 | Looi | A61F 2/07 623/1.16 |
| 2005/0131525 A1 | 6/2005 | Hartley | |
| 2005/0149163 A1* | 7/2005 | Sahota | 623/1.11 |
| 2005/0172471 A1 | 8/2005 | Vietmeier | |
| 2005/0222670 A1 | 10/2005 | Schaeffer | |
| 2005/0246008 A1 | 11/2005 | Hogendijk et al. | |
| 2005/0251164 A1 | 11/2005 | Gifford | |
| 2005/0278011 A1 | 12/2005 | Peckham | |
| 2005/0288764 A1* | 12/2005 | Snow et al. | 623/1.11 |
| 2005/0288766 A1* | 12/2005 | Plain et al. | 623/1.12 |
| 2006/0004433 A1* | 1/2006 | Greenberg et al. | 623/1.11 |
| 2006/0069424 A1* | 3/2006 | Acosta et al. | 623/1.12 |
| 2006/0074478 A1* | 4/2006 | Feller, III | 623/1.11 |
| 2006/0095113 A1 | 5/2006 | Niermann | |
| 2006/0111769 A1 | 5/2006 | Murray | |
| 2006/0136051 A1* | 6/2006 | Furst et al. | 623/1.42 |
| 2006/0149349 A1 | 7/2006 | Garbe | |
| 2006/0184225 A1 | 8/2006 | Pryor | |
| 2006/0184227 A1 | 8/2006 | Rust | |
| 2006/0193892 A1 | 8/2006 | Furst et al. | |
| 2006/0200231 A1* | 9/2006 | O'Brien et al. | 623/1.42 |
| 2006/0206190 A1 | 9/2006 | Chermoni | |
| 2006/0248698 A1 | 11/2006 | Hanson et al. | |
| 2006/0276871 A1* | 12/2006 | Lamson et al. | 623/1.11 |
| 2006/0282149 A1 | 12/2006 | Kao | |
| 2007/0021826 A1 | 1/2007 | Case et al. | |
| 2007/0088420 A1 | 4/2007 | Andreas et al. | |
| 2007/0093744 A1 | 4/2007 | Elmaleh | |
| 2007/0156223 A1 | 7/2007 | Vaughan | |
| 2007/0156225 A1 | 7/2007 | George et al. | |
| 2007/0179587 A1 | 8/2007 | Acosta et al. | |
| 2007/0191926 A1 | 8/2007 | Nikanorov et al. | |
| 2007/0233235 A1 | 10/2007 | Chouinard | |
| 2007/0255391 A1 | 11/2007 | Hojeibane et al. | |
| 2008/0033522 A1* | 2/2008 | Grewe et al. | 623/1.11 |
| 2008/0051867 A1 | 2/2008 | Davila et al. | |
| 2008/0077229 A1 | 3/2008 | Andreas et al. | |
| 2008/0082154 A1* | 4/2008 | Tseng et al. | 623/1.11 |
| 2008/0132999 A1 | 6/2008 | Mericle et al. | |
| 2008/0154355 A1* | 6/2008 | Benichou et al. | 623/1.26 |
| 2008/0208327 A1* | 8/2008 | Rowe | 623/2.11 |
| 2008/0221658 A1 | 9/2008 | Martin et al. | |
| 2008/0255653 A1 | 10/2008 | Schkolnik | |
| 2008/0264102 A1 | 10/2008 | Berra | |
| 2008/0319528 A1* | 12/2008 | Yribarren et al. | 623/1.15 |
| 2009/0076594 A1* | 3/2009 | Sabaria | A61F 2/82 623/1.34 |
| 2009/0082841 A1 | 3/2009 | Zacharias et al. | |
| 2009/0149943 A1 | 6/2009 | Tower | |
| 2009/0157159 A1* | 6/2009 | Schneider et al. | 623/1.11 |
| 2009/0171432 A1* | 7/2009 | Von Segesser et al. | 623/1.11 |
| 2009/0214615 A1 | 8/2009 | Zhao | |
| 2009/0216284 A1* | 8/2009 | Chin et al. | 606/86 R |
| 2009/0228088 A1 | 9/2009 | Lowe et al. | |
| 2009/0248139 A1* | 10/2009 | Pellegrini | A61F 2/91 623/1.17 |
| 2009/0248141 A1 | 10/2009 | Shandas et al. | |
| 2009/0270965 A1* | 10/2009 | Sinha et al. | 623/1.11 |
| 2009/0270967 A1* | 10/2009 | Fleming, III et al. | 623/1.11 |
| 2009/0276031 A1 | 11/2009 | Kao | |
| 2010/0042121 A1 | 2/2010 | Schneider et al. | |
| 2010/0042204 A1* | 2/2010 | O'Brien et al. | 623/1.15 |
| 2010/0131045 A1* | 5/2010 | Globerman | A61F 2/91 623/1.16 |
| 2010/0137966 A1 | 6/2010 | Magnuson | |
| 2010/0228333 A1 | 9/2010 | Drasler et al. | |
| 2010/0298921 A1* | 11/2010 | Schlun | A61F 2/91 623/1.2 |
| 2010/0318173 A1 | 12/2010 | Kolandaivelu et al. | |
| 2011/0004237 A1* | 1/2011 | Schneider et al. | 606/194 |
| 2011/0077731 A1 | 3/2011 | Lee et al. | |
| 2011/0125248 A1 | 5/2011 | George et al. | |
| 2011/0152992 A1 | 6/2011 | Schneider et al. | |
| 2011/0230954 A1 | 9/2011 | Schneider et al. | |
| 2011/0301690 A1 | 12/2011 | Giasolli et al. | |
| 2012/0016457 A1 | 1/2012 | Chobotov et al. | |
| 2012/0035705 A1 | 2/2012 | Giasolli et al. | |
| 2012/0083872 A1 | 4/2012 | Schneider et al. | |
| 2012/0191176 A1 | 7/2012 | Nagl et al. | |
| 2013/0144375 A1 | 6/2013 | Giasolli et al. | |
| 2014/0081380 A1 | 3/2014 | Giasolli et al. | |
| 2014/0194967 A1 | 7/2014 | Schneider et al. | |
| 2014/0288629 A1 | 9/2014 | Amendt | |
| 2017/0000629 A1 | 1/2017 | Giasolli et al. | |
| 2017/0181873 A1 | 6/2017 | Schneider et al. | |
| 2017/0296366 A1 | 10/2017 | Giasolli et al. | |
| 2017/0319361 A1 | 11/2017 | Giasolli et al. | |
| 2017/0319364 A1 | 11/2017 | Jung et al. | |
| 2018/0110634 A1 | 4/2018 | Giasolli et al. | |
| 2018/0200085 A1 | 7/2018 | Giasolli et al. | |
| 2018/0200086 A1 | 7/2018 | Giasolli et al. | |
| 2018/0200087 A1 | 7/2018 | Giasolli et al. | |
| 2018/0207007 A1 | 7/2018 | Giasolli et al. | |
| 2018/0207008 A1 | 7/2018 | Giasolli et al. | |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 101262835 | 9/2008 |

(56) References Cited

FOREIGN PATENT DOCUMENTS

| | | |
|---|---|---|
| CN | 101754727 | 6/2010 |
| CN | 102724931 | 10/2012 |
| CN | 103313682 | 9/2013 |
| CN | 104220026 | 12/2014 |
| CN | 104887365 | 9/2015 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 104887365 | 12/2017 |
| DE | 60030705 | 5/2007 |
| DE | 10 2009 041 025 | 3/2011 |
| DE | 20 2011 107 781 | 12/2011 |
| DE | 20 2011 110 714 | 12/2015 |
| DE | 10 2014 016 588 | 5/2016 |
| DE | 20 2011 110 818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1803423 | 7/2007 |
| EP | 1894545 | 3/2008 |
| EP | 2219535 | 8/2010 |
| EP | 2440155 | 4/2012 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 3072463 | 9/2016 |
| EP | 2775968 | 9/2017 |
| EP | 3217927 | 9/2017 |
| FR | 2714816 | 7/1995 |
| GB | 201106757 | 6/2011 |
| JP | H11-501526 | 2/1999 |
| JP | H11-506665 | 6/1999 |
| JP | 2007-503923 | 3/2007 |
| JP | 2008-504078 | 2/2008 |
| JP | 2008-246214 | 10/2008 |
| JP | 2008-537891 | 10/2008 |
| JP | 2015-506760 | 3/2015 |
| JP | 2016-135278 | 7/2016 |
| JP | 6006808 | 10/2016 |
| KR | 10-2017-0084214 | 7/2017 |
| WO | WO 1996/009013 | 3/1996 |
| WO | WO 1996/037167 | 11/1996 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 2003/047651 | 6/2003 |
| WO | WO 03/101310 A1 | 12/2003 |
| WO | WO03101310 | 12/2003 |
| WO | WO 2004/006983 | 1/2004 |
| WO | WO 2004/032799 | 4/2004 |
| WO | WO 2006/026371 | 3/2006 |
| WO | WO 2007/088549 | 8/2007 |
| WO | WO 2007088549 A2 * | 8/2007 ....... A61B 17/12022 |
| WO | WO 2007/109621 | 9/2007 |
| WO | WO 2009/076517 | 6/2009 |
| WO | WO 2010/037141 | 4/2010 |
| WO | WO 2010/118432 | 10/2010 |
| WO | WO 2010/144845 | 12/2010 |
| WO | WO 2011/153110 | 12/2011 |
| WO | WO 2012/006602 | 1/2012 |
| WO | WO 2012/143731 | 10/2012 |
| WO | WO 2013/068127 | 5/2013 |
| WO | WO 2013/112768 | 8/2013 |
| WO | WO 2016/074799 | 5/2016 |

OTHER PUBLICATIONS

Supplemental Office Action for Australian Application No. 2008335140 dated Apr. 21, 2011.
Supplementary Partial European Search Report for European Application No. EP08858824.9 dated Sep. 27, 2012.
Colombo et al., "Intravascular Ultrasound-Guided Percutaneous Transluminal Coronary Angioplasty With Provisional Spot Stenting for Treatment of Long Coronary Lesions", Journal of the American College of Cardiology, vol. 38, No. 5, Nov. 1, 2001.
Australian Office Action (Notice of Acceptance), re AU Application No. 2011274392, dated Nov. 14, 2013, including accepted (allowed) claims.
Australian Office Action, re AU Application No. 2008335140, dated Mar. 15, 2011.
Australian Office Action, re AU Application No. 2011274392, dated May 3, 2013.
European Office Action and Supplemental European Search Report, re EP Application No. 11804455.1, dated Jun. 11, 2014.
International Search Report and Written Opinion, re PCT Application No. PCT/US2010/038379, dated Feb. 25, 2011.
International Search Report and Written Opinion, re PCT Application No. PCT/US2011/038468, dated Jan. 18, 2012.
International Search Report and Written Opinion, re PCT Application No. PCT/US2013/023030, dated Apr. 16, 2013.
International Search Report and Written Opinion, re PCT Application PCT/US2008/086396, dated Jul. 27, 2009.
International Search Report and Written Opinion, re PCT Application PCT/US2011/043471, dated Feb. 9, 2012.
International Search Report, re PCT Application No. PCT/US2013/023030, dated Apr. 16, 2013.
Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.
Kokkinidis, D. et al., "Emerging and Future Therapeutic Options for Femoropopliteal and Infrapopliteal Endovascular Intervention", Interventional Cardiology Clinics, vol. 6, 2017, in 17 pages.
Shishehbor, M. et al., "Endovascular Treatment of Femoropopliteal Lesions", Journal of the Americal College of Cardiology, vol. 66, 2015, in 4 pages.
Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.
International Preliminary Report on Patentability, re PCT Application No. PCT/US2008/086396, dated Jun. 15, 2010.
International Preliminary Report on Patentability, re PCT Application No. PCT/US2011/038468, dated Dec. 13, 2012.
International Preliminary Report on Patentability, re PCT Application No. PCT/US2011/043471, dated Jan. 17, 2013.
International Preliminary Report on Patentability, re PCT Application No. PCT/US2013/023030, dated Aug. 7, 2014.
U.S. Appl. No. 11/955,331, filed Dec. 12, 2007, (U.S. Pat. No. 7,896,911), (Mar. 1, 2011), Device and Method for Tacking Plaque to Blood Vessel Wall.
U.S. Appl. No. 15/375,026, filed Dec. 9, 2016, Device and Method for Tacking Plaque to Blood Vessel Wall.
U.S. Appl. No. 13/038,175, filed Mar. 1, 2011, (U.S. Pat. No. 9,545,322), (Jan. 17, 2017), Device and Method for Tacking Plaque to Blood Vessel Wall.
U.S. Appl. No. 12/483,193, filed Jun. 11, 2009, (U.S. Pat. No. 8,128,677), (Mar. 6, 2012), Device and Method for Tacking Plaque to a Blood Vessel Wall.
U.S. Appl. No. 13/246,776, filed Sep. 27, 2011, (U.S. Pat. No. 9,974,670), (May 22, 2018), Method of Treating Atherosclerotic Occlusive Disease.

(56) References Cited

OTHER PUBLICATIONS

U.S. Appl. No. 15/984,111, filed May 18, 2018, Method of Treating Atherosclerotic Occlusive Disease.
U.S. Appl. No. 14/102,411, filed Dec. 10, 2013, Method of Treating Atherosclerotic Occlusive Disease.
U.S. Appl. No. 12/790,819, filed May 29, 2010, Minimal Surface Area Contant Device for Holding Plaque to Blood Vessel Wall.
U.S. Appl. No. 13/118,388, filed May 28, 2011, Stent Device Having Focal Elevating Elements for Minimal Surface Area Contact With Lumen Walls.
U.S. Appl. No. 13/179,458, filed Jul. 8, 2011, (U.S. Pat. No. 10,022,250), (Jul. 17, 2018), Deployment Device for Placement of Multiple Intraluminal Surgical Staples.
U.S. Appl. No. 15/815,515, filed Nov. 16, 2017, Deployment Device for Placement of Multiple Intraluminal Surgical Staples.
U.S. Appl. No. 15/921,464, filed Mar. 14, 2018, Deployment Device for Placement of Multiple Intraluminal Surgical Staples.
U.S. Appl. No. 13/153,257, filed Jun. 3, 2011, (U.S. Pat. No. 9,375,327), (Jun. 28, 2016), Endovascular Implant.
U.S. Appl. No. 15/170,772, filed Jun. 1, 2016, Endovascular Implant.
U.S. Appl. No. 15/640,095, filed Jun. 30, 2017, Endovascular Implant.
U.S. Appl. No. 15/921,448, filed Mar. 14, 2018, Endovascular Implant.
U.S. Appl. No. 15/921,459, filed Mar. 14, 2018, Endovascular Implant.
U.S. Appl. No. 15/921,477, filed Mar. 14, 2018, Endovascular Implant.
U.S. Appl. No. 13/749,643, filed Jan. 24, 2013, (U.S. Pat. No. 9,730,818), (Aug. 15, 2017), Endoluminal Device and Method.
U.S. Appl. No. 14/089,703, filed Nov. 25, 2013, (U.S. Pat. No. 9,603,730), (Mar. 28, 2017), Endoluminal Device and Method.
U.S. Appl. No. 15/472,215, filed Mar. 28, 2017, Endoluminal Device and Method.
U.S. Appl. No. 15/654,586, filed Jul. 19, 2017, Endoluminal Device and Method.
U.S. Appl. No. 15/837,870, filed Dec. 11, 2017, Endoluminal Device and Method.
U.S. Appl. No. 15/921,541, filed Mar. 14, 2018, Endoluminal Device and Method.
U.S. Appl. No. 13/939,019, filed Jul. 10, 2013, Systems and Methods for Attaching Radiopaque Markers to a Medical Device.
U.S. Appl. No. 14/746,636, filed Jun. 22, 2015, (U.S. Pat. No. 9,192,500), (Nov. 24, 2015), Delivery Device and Method of Delivery.
U.S. Appl. No. 14/885,295, filed Jun. 22, 2015, (U.S. Pat. No. 9,375,337), (Jun. 28, 2016), Delivery Device and Method of Delivery.
U.S. Appl. No. 15/133,709, filed Apr. 20, 2016, Delivery Device and Method of Delivery.
U.S. Appl. No. 14/935,087, filed Nov. 6, 2015, (U.S. Pat. No. 9,345,603), (May 24, 2016), Delivery Device and Method of Delivery.
U.S. Appl. No. 15/133,751, filed Apr. 20, 2016, (U.S. Pat. No. 9,602,786), (Mar. 21, 2017), Delivery Device and Method of Delivery.
U.S. Appl. No. 14/935,121, filed Nov. 6, 2015, (U.S. Pat. No. 9,320,632), (Apr. 26, 2016), Delivery Device and Method of Delivery.
U.S. Appl. No. 15/133,158, filed Apr. 19, 2016, (U.S. Pat. No. 9,584,777), (Feb. 28, 2017), Delivery Device and Method of Delivery.
U.S. Appl. No. 15/011,321, filed Jan. 29, 2016, (U.S. Pat. No. 9,456,914), (Oct. 4, 2016), Delivery Device and Method of Delivery.
U.S. Appl. No. 15/134,315, filed Apr. 20, 2016, (U.S. Pat. No. 9,585,782), (Mar. 7, 2017), Delivery Device and Method of Delivery.
U.S. Appl. No. 15/415,167, filed Jan. 25, 2017, Delivery Device and Method of Delivery.
U.S. Appl. No. 14/656,462, filed Mar. 12, 2015, (U.S. Pat. No. 9,375,336), (Jun. 28, 2016), Delivery Device and Method of Delivery.
U.S. Appl. No. 14/935,154, filed Nov. 6, 2015, (U.S. Pat. No. 9,445,929), (Sep. 20, 2016), Delivery Device and Method of Delivery.
U.S. Appl. No. 15/194,410, filed Jun. 27, 2016, Delivery Device and Method of Delivery.
U.S. Appl. No. 15/000,437, filed Jan. 19, 2016, (U.S. Pat. No. 9,433,520), (Sep. 6, 2016), Delivery Device and Method of Delivery.
U.S. Appl. No. 15/227,757, filed Aug. 3, 2016, Delivery Device and Method of Delivery.
U.S. Appl. No. 16/067,082, filed Jun. 28, 2018, Delivery Device and Method of Delivery.
U.S. Appl. No. 15/705,793, filed Sep. 15, 2017, Delivery Device and Method of Delivery.

* cited by examiner

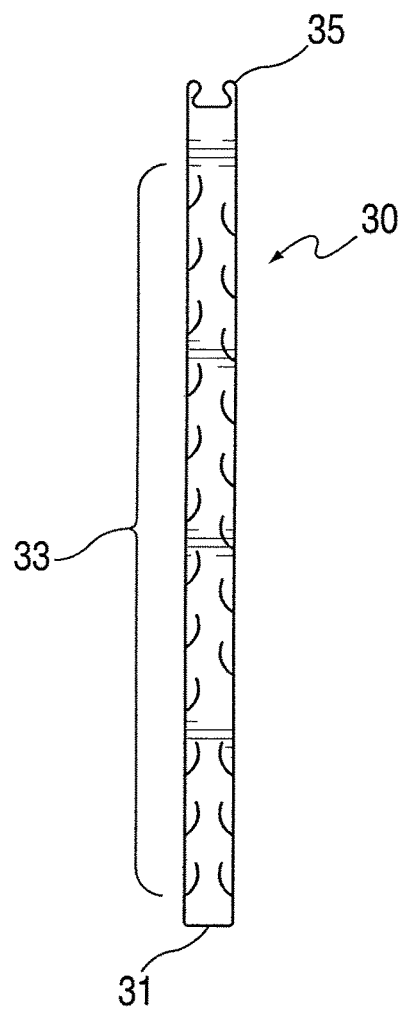 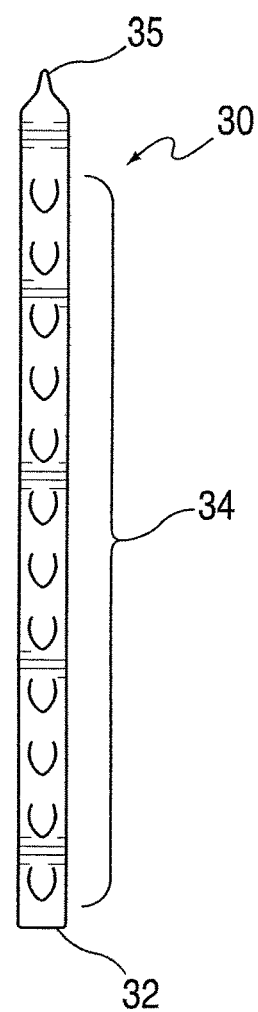
FIG. 1A    FIG. 1B
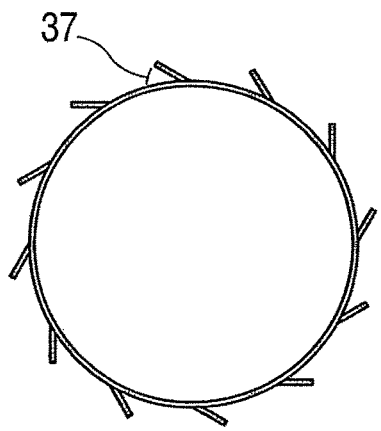 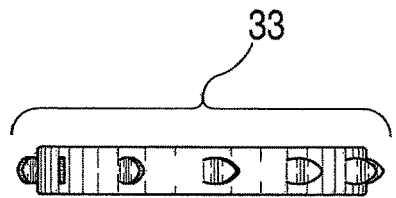
FIG. 2    FIG. 3

FEE

FEE

FIG. 39
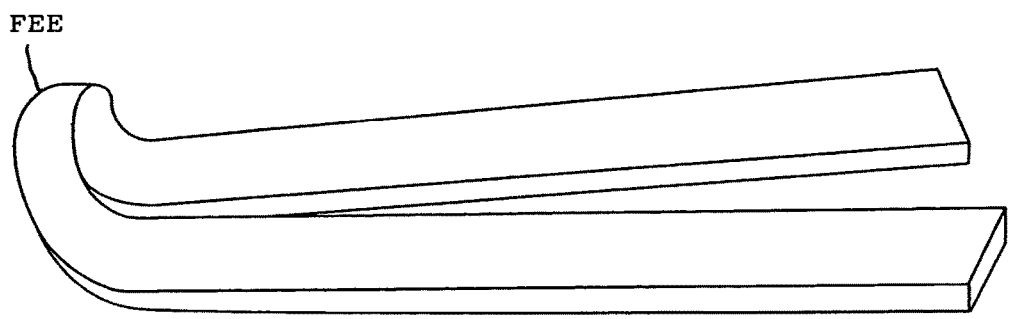
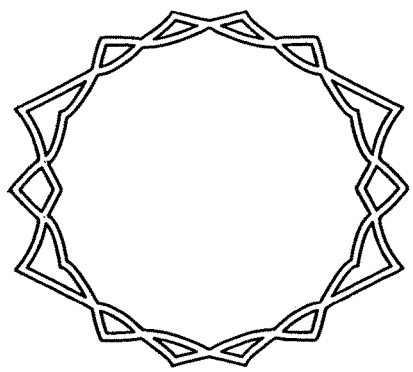
FIG. 40A
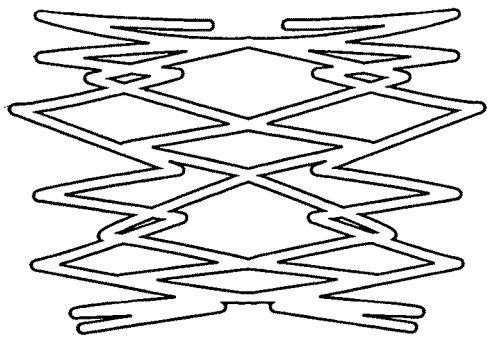
FIG. 40B

MINIMAL SURFACE AREA CONTACT DEVICE FOR HOLDING PLAQUE TO BLOOD VESSEL WALL

This invention disclosure is a continuation-in-part of previously U.S. patent application Ser. No. 12/483,193, filed Jun. 11, 2009 and issued as U.S. Pat. No. 8,128,677, of the same inventors.

TECHNICAL FIELD

This invention relates to treatment of atherosclerotic occlusive disease by intravascular procedures for pushing and holding plaque accumulated on the blood vessel walls out of the way for reopened blood flow.

BACKGROUND OF INVENTION

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty form dissection. A dissection occurs when a portion of the plaque is lifted away from the artery and is not fully adherent and may be mobile or loose. The plaque that has been disrupted by dissection protrudes into the flowstream. If the plaque lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is better to place a metal retaining structure, such as stent to hold open the artery after angioplasty and force the dissected material back against the wall of the blood vessel to create an adequate lumen for blood flow.

Therefore, the clinical management of dissection after balloon angioplasty is currently performed primarily with stents. As illustrated in FIG. 24A, a stent is a tube having a diameter that is sized to the artery. A stent is placed into the artery at the location of a dissection to force the dissection flap against the inner wall of the blood vessel. Stents are usually made of metal alloys. They have varying degrees of flexibility, visibility, and different placement techniques. Stents are placed in every vascular bed in the body. The development of stents has significantly changed the approach to minimally invasive treatment of vascular disease, making it safer and in many cases more durable. The incidence of acute occlusion after balloon angioplasty has decreased significantly with stents.

However, stents have significant disadvantages and much research and development is being done to address these issues. Stents induce repeat narrowing of the treated blood vessel (recurrent stenosis). Recurrent stenosis is the "Achilles heel" of stenting. Depending on the location and the size of the artery, in-growth of intimal hyperplastic tissue from the vessel wall in between struts or through openings in the stent may occur and cause failure of the vascular reconstruction by narrowing or occlusion of the stent. This may occur any time after stent placement. In many cases, the stent itself seems to incite local vessel wall reaction that causes stenosis, even in the segment of the stent that was placed over artery segments that were not particularly narrowed or diseased during the original stent procedure. This reaction of the blood vessel to the presence of the stent is likely due to the scaffolding effect of the stent. This reaction of recurrent stenosis or tissue in growth of the blood vessel is in response to the stent. This activity shows that the extensive use of metal and vessel coverage in the artery as happens with stenting is contributing to the narrowing. The recurrent stenosis is a problem because it causes failure of the stent and there is no effective treatment. Existing treatment methods that have been used for this problem include; repeat angioplasty, cutting balloon angioplasty, cryoplasty, atherectomy, and even repeat stenting. None of these methods have a high degree of long-term success.

Stents may also fracture due to material stress. Stent fracture may occur with chronic material stress and is associated with the development of recurrent stenosis at the site of stent fracture. This is a relatively new finding and it may require specialized stent designs for each application in each vascular bed. Structural integrity of stents remains a current issue for their use. Arteries that are particularly mobile, such as the lower extremity arteries and the carotid arteries, are of particular concern. The integrity of the entire stent is tested any time the vessel bends or is compressed anywhere along the stented segment. One reason why stent fractures may occur is because a longer segment of the artery has been treated than is necessary. The scaffolding effect of the stent affects the overall mechanical behavior of the artery, making the artery less flexible. Available stenting materials have limited bending cycles and are prone to failure at repeated high frequency bending sites.

Many artery segments are stented even when they do not require it, thereby exacerbating the disadvantages of stents. There are several reasons for this. Many cases require more than one stent to be placed and often several are needed. Much of the stent length is often placed over artery segments that do not need stenting and are merely adjoining an area of dissection or disease. Stents that are adjusted to the precise length of the lesion are not available. When one attempts to place multiple stents and in the segments most in need of stenting, the cost is prohibitive since installation and material is required per stent. The time it takes to do this also adds to the cost and risk of the procedure. The more length of artery that receives a stent that it does not need, the more stiffness is conferred to the artery, and the more scaffolding affect occurs. This may also help to incite the arterial reaction to the stent that causes recurrent stenosis.

SUMMARY OF INVENTION

In accordance with the present invention, a tack device (and related method of deployment) for treating atherosclerotic occlusive disease comprises an annular band of durable, flexible material configured to be radially expandable outwardly under a spring or other expansion force and having a plurality of focal elevating elements on its outer annular periphery. The tack device is inserted in the blood vessel in a compressed state and installed in an expanded state by a catheter delivery mechanism after a balloon angioplasty procedure at one or more specific positions of loose plaque against the blood vessel wall. The focal elevating elements are designed to exert a holding force under expansion force pressure on the plaque while minimizing the amount of material surface area in contact with the plaque or blood vessel wall.

The annular band of the plaque tack has a width in the axial (length) direction of the vessel walls that is about equal to or less than its diameter, in order to minimize the emplacement of foreign scaffolding structure in the blood vessel. One or more tacks are applied only in positions along the length of a plaque accumulation site where specific holding forces are needed to stabilize the site and/or hold pieces of plaque out of the way of blood flow. The focal elevating elements of the tack(s) may be pressed with an expansion force into the plaque and/or vessel walls, for example, by a post-installation balloon expansion procedure.

In the present invention, the plaque tack device is designed as a minimally invasive approach to tacking loose or dissected atherosclerotic plaque to the wall of the artery, as illustrated in FIG. 24B. It may be used to treat either de novo atherosclerotic lesions or the inadequate results of balloon angioplasty. It is designed to maintain adequate lumen in a treated artery without the inherent disadvantages of vascular stents. The device may also be used to administer medications, fluid, or other treatment ("eluting") agents into the atherosclerotic plaque or the wall of the blood vessel or into the bloodstream.

The plaque tack and installation procedure may be designed in a number of ways that share a common methodology of utilizing an expansion force of the delivery mechanism (such as balloon expansion) and/or the expansion force of a compressible annular band to enable the tack to be moved into position in the blood vessel, then released, unfolded or unplied to expand to its full diametral size within the blood vessel walls.

In a preferred embodiment, the tack device comprises a thin, annular band of durable, flexible material having a plurality of focal elevating elements on its outer annular periphery, said annular band being dimensioned and designed to be applied with an expansion force against the plaque to press and hold the plaque at an applied site of said band against the blood vessel walls. Besides stabilizing the emplacement of the tack, the focal elevating elements play a role in tacking the plaque to the blood vessel wall. The annular band has a length in the axial direction of the blood vessel walls that is about equal to or less than its diameter when expanded. In a ring or ribbon-shaped form, the annular band can have a ratio of length to diameter as low as 1/100. The plaque tack device can also have a structure for carrying medication such that it elutes a biologically active agent to the plaque to inhibit growth and/or for treating the blood vessel wall.

For all embodiments an important parameter characterizing design of a plaque tack is the ratio: Vessel Coverage Area (C) to Total Vessel Surface area (TVS), where C/TVS is less than or equal to about 60%. This equation can be applied to one tack device or when several spaced-apart tack devices are placed across the length of a blood vessel treatment area.

In another preferred embodiment, a tack device is formed with concentric side rings or mesh bands connected by longitudinal bridge members. As adapted from a measure of Relative Metal Surface Area (RMS) compared to the number of longitudinal segments in the device structure, an equation for Effective Metallic Interface (EMI) may be used to compare this embodiment of the tack device to a typical stent, as follows:

$$EMI = \frac{(1+n^2)C}{\sum_{s=1}^{x}(lw)_s}$$

where x is the number of sections of metal, l is an individual metal section length, w is an individual metal section width, C is the vessel coverage area underneath the device (lumen surface), and n is the number of bridge members longitudinally connected between circumferentially oriented segments. The summation found in the denominator can be interpreted as the total metal surface area. The preferred embodiment of the tack device has an EMI≤10, whereas the EMI of a typical stent would be several times greater.

To further reduce the EMI through the inclusion of lift-off-bump (FEE) features, an improved $EMI_F$ can be obtained for the Tack Effective Metal Interface as provided with floating elements (see FIG. 27). $EMI_F$ can be defined as:

$$EMI_F = \frac{C(1+(n-n_F)^2)}{\sum_{S=1}^{x}(lw-l_Fw_F)_S}$$

where all variables are the same as those in the EMI equation with the addition of $l_F$ is an individual metal section length that is not in contact with the artery (floating off the artery), and $w_F$ is the width of the same section. If no floating sections exist then $n_F=0$ and $l_Fw_F=0$ and therefore $EMI_F=EMI$.

The present invention also encompasses the method of using the tack device to treat any plaque dissection in the blood vessel after balloon angioplasty by installing it with an expansion force against the plaque to hold it against the blood vessel walls. One preferred method encompasses one wherein drug eluting balloon angioplasty is first performed, and if there is any damage, disruption, dissection, or irregularity to the blood vessel caused by the balloon angioplasty mechanism, one or more tack devices may be used to tack down the damaged, disrupted, dissected, or irregular blood vessel surface, so as to avoid the need to install a stent and thereby maintain a 'stent-free' environment.

Other objects, features, and advantages of the present invention will be explained in the following detailed description of the invention having reference to the appended drawings.

BRIEF DESCRIPTION OF DRAWINGS

FIGS. 1A and 1B are schematic diagrams of an embodiment in ribbon form for the plaque tack device.

FIG. 2 is a side view of the first embodiment of the ribbon tack of FIG. 1B in its annular shape after deployment.

FIG. 3 is a plan view of the ribbon tack of FIG. 1B in its annular shape after deployment.

FIGS. 29A and 29B illustrate the use of focal elevating elements with barbs on a tack device having two or more concentric ring sections joined by bridges in between.

FIGS. 32-39 illustrate variations in forming and positioning focal elevating elements on strut sections of a tack device.

FIGS. 40A and 40B show a detailed view of the preferred embodiment of the plaque tack formed with concentric rings containing focal elevating elements at the apexes of the long struts and sets of barbs at the bridges.

DETAILED DESCRIPTION OF INVENTION

The subject matter of this invention disclosure is directed to the improvement of an annular tack device having focal elevating elements on its annular periphery to minimize surface area contact and reduce friction generated at contact areas between tack device and the blood vessel wall. The improvement of the present invention disclosure is a continuation-in-part of the original disclosure of previous preferred embodiments of an annular tack device having barbs on its annular periphery for holding loose plaque under expansion force against a blood vessel wall. In the following description, the previous preferred embodiments are first described to illustrate specific examples and details of their implementation. A description of preferred embodiments of the improvement of the annular tack device with focal elevating elements then follows.

Figure 24A:
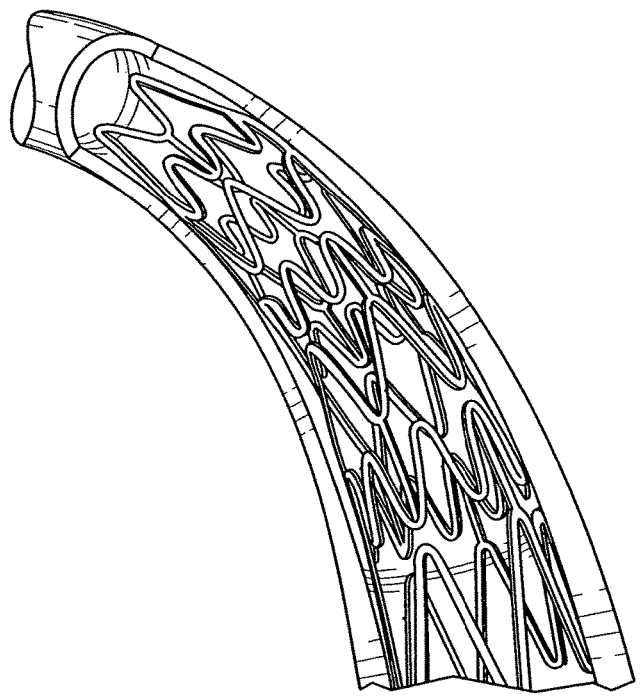
FIG. 24A illustrates the use of a stent installed after angioplasty as conventionally practiced in the prior art.
Figure 24B:
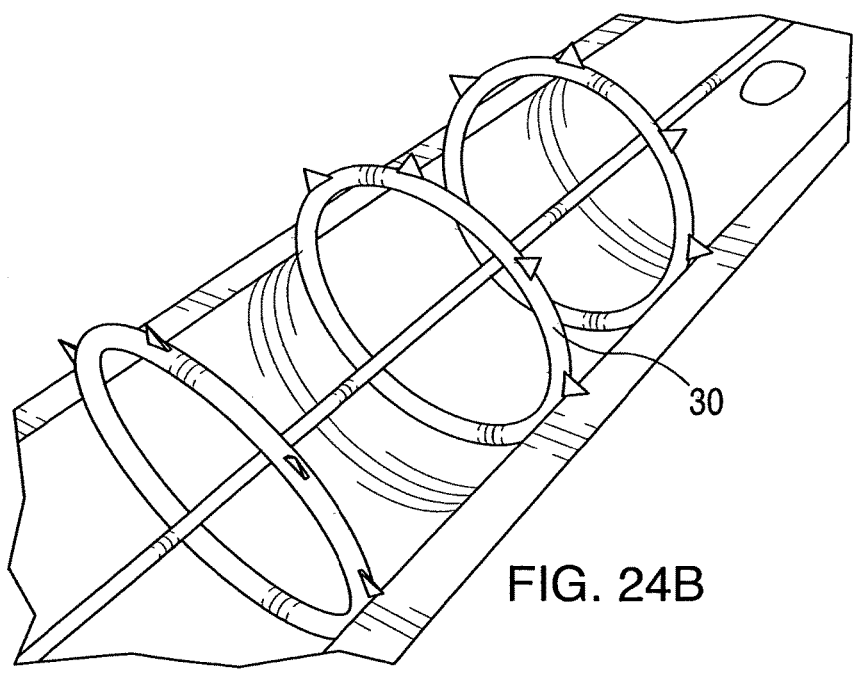
FIG. 24B illustrates the use of the plaque tack installed after angioplasty demonstrating its advantages over the prior art.

As illustrated in FIG. 24B, the previous plaque tack device generally comprises a thin, annular band of durable, flexible material having a plurality of barbs or anchoring elements on its outer annular periphery. The plaque tack is dimensioned diametrally and is designed to be applied with an expansion force against the plaque to press and hold it against the blood vessel walls. The barbs or anchoring elements are embedded into or at least emplaced in physical contact against the plaque by the expansion force of the plaque tack. The plaque tack extends over only a small area in the axial direction of the vessel walls, in order to minimize the amount of foreign structure placed in the blood vessel. One or more tacks are applied only in positions along the length of a plaque accumulation site where specific holding forces are needed to stabilize the site and/or hold pieces of plaque out of the way of blood flow.

The plaque tack and installation procedure may be designed in a number of ways that share a common methodology of utilizing the outward force of a spring-like annular band to enable the tack to be compressed, folded, or plied to take up a small-diameter volume so that it can be moved into position in the blood vessel on a sheath or catheter, then released, unfolded or unplied to expand to its full-diametral size within the blood vessel walls.

In the following description, five general embodiments of the plaque tack device and how to deliver it are explained in detail, referred to as: (1) ribbon tack; (2) folding ring tack; (3) flexible ring tack; (4) spiral coil tack; and (5) metallic mesh tack. All these embodiments are delivered into the blood vessel from endovascular insertion. The delivery device for each involves a delivery apparatus that has some features of a vascular sheath. The delivery device for each is different and has features that are specifically designed to deliver the specific tack Referring to FIGS. 1A and 1B, a first preferred embodiment of the plaque tack device is shown in two versions of a ribbon tack, each having a linear, flat shape like a ribbon. The version in FIG. 1A has a base end 31, rows 33 of cutout tongues or apertured portions that open out as pointed barbs or anchors, and a retainer end 35. The version in FIG. 1B has a base end 32, single row 34 of cutout portions that open out as pointed barbs or anchors, and a retainer end 35. Each version may be made of a material such as a corrosion-resistant metal, polymer, composite or other durable, flexible material. A preferred material is a metal having "shape-memory" (such as Nitinol) which allows it to be formed initially with an annular shape prior to forming in a linear shape, then resume the annular shape when exposed for a length of time at internal body temperature. When the strip is deployed in the blood vessel, it is curved into an annular shape. FIG. 2 shows the view of the strip of material in FIG. 1B after it is curved into its preferred shape of deployment in the blood vessel, leaving a large inner, open area 36 for blood flow through it. The barbs are shown opened to outwardly pointing angles 37 due to bending forces so that they point toward the wall or surface of the blood vessel.

In a typical configuration, the ribbon tack may have a width of about 0.1 to 5 mm, a diameter (when curved in annular shape) of about 1 to 10 mm, a length (when extended linearly) of about 3 to 30 mm, and a barb height from 0.01 to 5 mm. In general, the annular band of the plaque tack has a width in the axial direction of the vessel walls that is about equal to or less than its diameter, in order to minimize the amount of foreign structure to be emplaced in the blood vessel. For tack designs in a ring or ribbon shape, the strut width to ring diameter ratio can be in the range of 1/10 to 1/100.

Figure 4A:
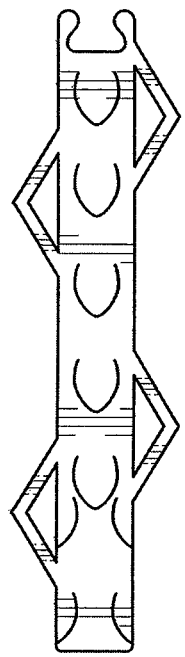
FIG. 4 is an alternative version of the ribbon tack of FIG. 1B having stabilizing wings.
Figure 4B:
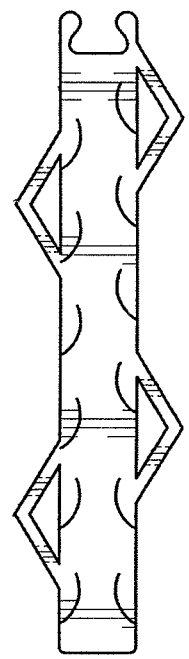
Figure 8:
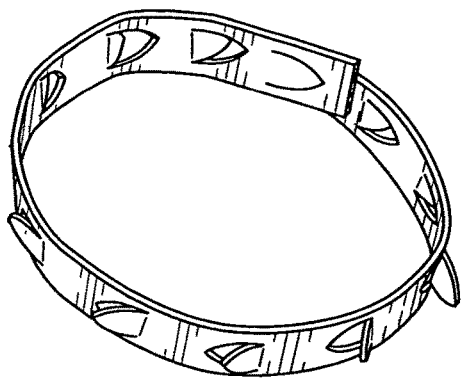
FIG. 8 is a photo image of the ribbon tack of FIG. 1B showing the tongues or cutout portions protruding at an angle from the metal strip when the tack is bent into an annular shape.
Figure 9:
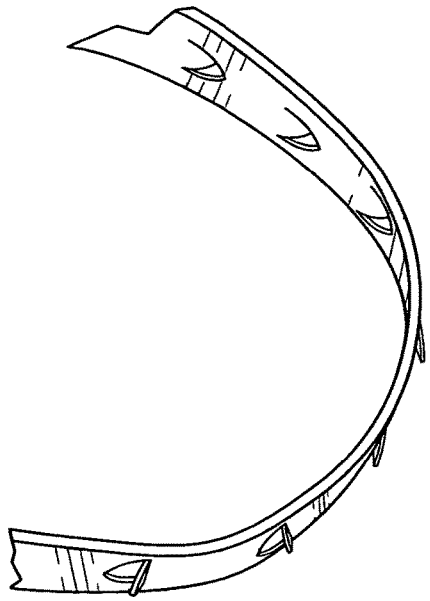
FIG. 9 is a close-up image of the elevating elements of the ribbon tack of FIG. 1B.
Figure 10:
FIG. 10 is a photo image of the ribbon tack of FIG. 1B prior to installation.

FIG. 3 is a schematic diagram showing a top view of the ribbon tack bent into its annular shape. FIG. 4 shows an alternative version of the ribbon tack having stabilizing wings provided along its side edges for added lateral stability when deployed in the blood vessel. FIG. 8 shows an overhead photo image of the ribbon tack with anchors protruding at an outward angle. FIG. 9 is a close-up image of the anchors of the annular strip. FIG. 10 is an overhead image of the metal strip extended linearly when at rest.

Figure 11:
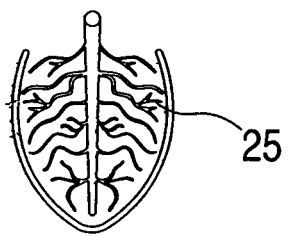
FIG. 11 illustrates a pattern of capillaries formed on the tongues of the ribbon tack of FIG. 1B for delivering plaque-growth retarding material into the plaque.
Figure 12:
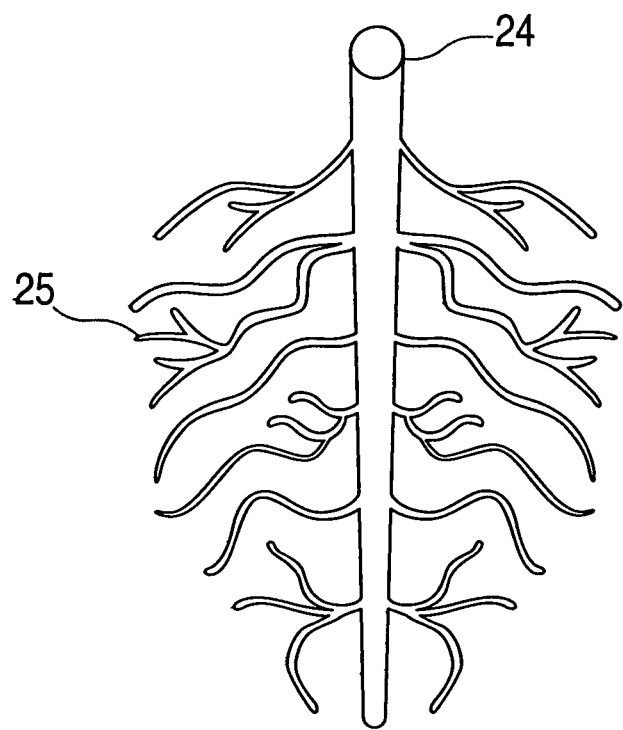
FIG. 12 is a close-up view of the capillaries formed on the tongues of the ribbon tack in FIG. 11.

FIG. 11 illustrates a pattern of capillaries 25 that may be formed by etching the surfaces of the tongues or cutout portions for delivering plaque-growth retarding material or other treatment agent where the tack is installed at the plaque accumulation site. FIG. 12 illustrates how the pattern of capillaries 25 is supplied with plaque-retarding or treatment material through a supply conduit 24. The material may be either resident within the channels prior to insertion of the tack or transferred from a reservoir on the inside of the annulus, through a hole to the outside of the component on the surface, into the anchored object, and into the tissue wall, enabling delivery of a treatment or such that enables additional preventative measures for retaining optimal blood flow. The forces that enable the transfer of the material from the inside of the annulus through the tree branches might be either capillary force or a combination of capillary and hydraulic pressure. Capillary action, capillarity, capillary motion, or wicking is the ability of a substance to draw another substance into it. The standard reference is to a tube in plants but can be seen readily with porous paper. It occurs when the adhesive intermolecular forces between the liquid and a substance are stronger than the cohesive intermolecular forces inside the liquid. The effect causes a concave meniscus to form where the substance is touching a vertical surface.

The array of barbs or elevating elements is used for linking the annular band of the tack with the plaque mass or blood vessel wall. The barb is made of a sufficiently rigid material to sustain a locking relationship with the blood vessel tissue and/or to pierce the plaque and maintain a locking relationship therewith. The barb is comprised of a head disposed on a support body. Preferably, the head and support body are integral with each other and are constructed as a single piece. The barb may project at an angle of 90 degrees to the tangent of the annular band, or an acute angle may also be used.

Figure 13:
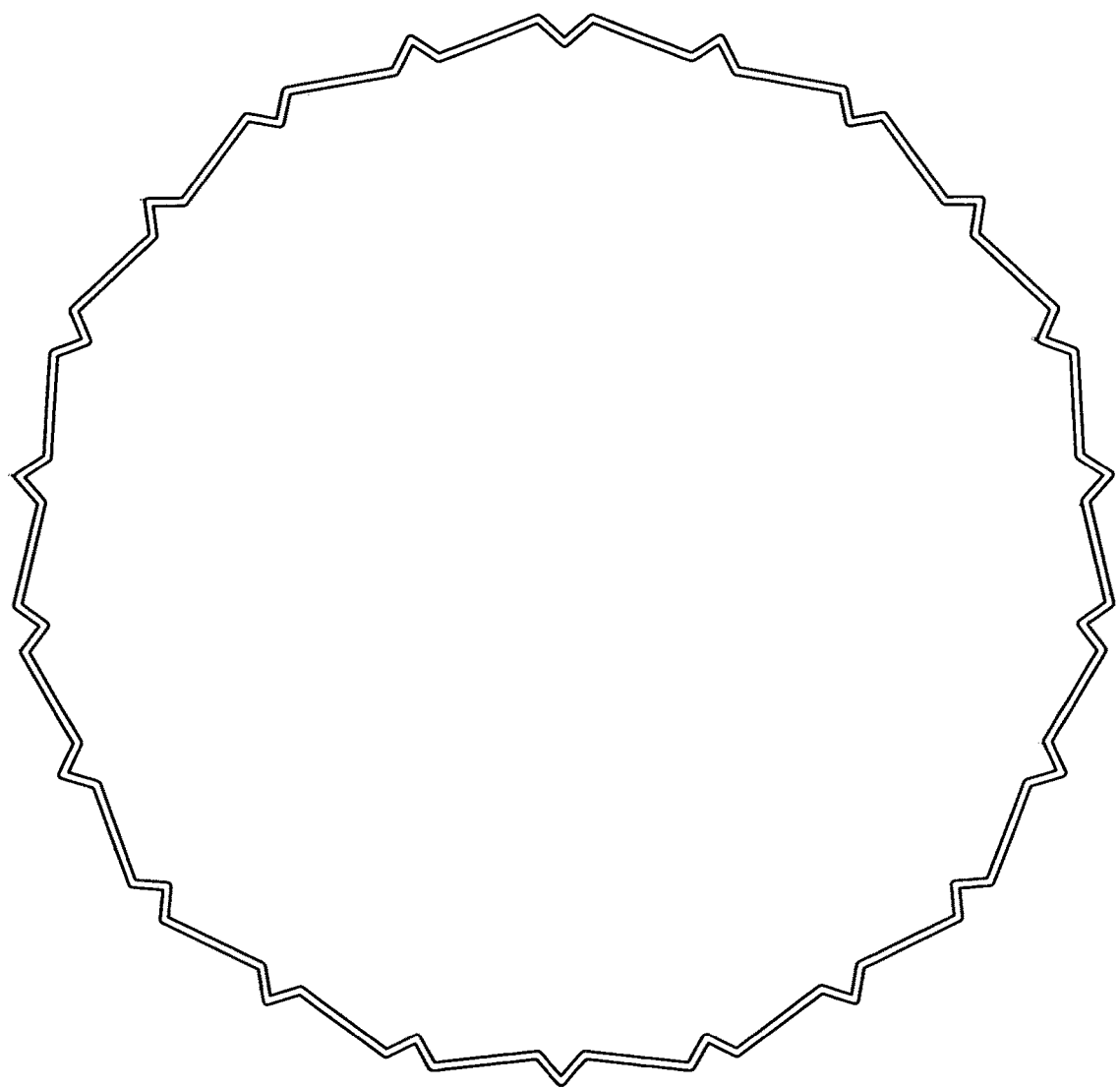
FIG. 13 is a schematic diagram of another embodiment of a folding ring tack having inner V-shaped segments for folding and outer inverted-V-shaped points for anchoring.

Referring to FIG. 13, a second preferred embodiment of the previous plaque tack device is formed as a folding ring tack having inner V-shaped segments for folding alternating with outer inverted-V-shaped points. The V-shaped segments allow the ring to be radially folded to a small-diameter volume for carriage on a deployment tube on the end of the sheath. At the desired position in the blood vessel, the compressed ring tack is released from the deployment tube so that the ring springs out to its full diametral shape and the outward points act as barb or elevating elements embedded into or pressed against the plaque. The folding ring tack is preferably made of metal wire material. Other options for the shape of the anchors on the outer surface may be used.

Figure 5:
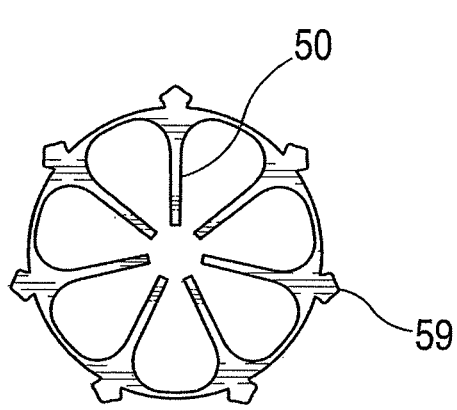
FIG. 5 is a schematic diagram of another embodiment of a flexing star tack having outward triangular elevating elements and inward radial fingers.

Referring to FIG. 5, a third preferred embodiment of the plaque tack device is formed as a flexible ring tack having a pliable or hinged structure and formed with an array of radially extending points 59 on an outer side of the ring, and an array of inner radial fingers 50. The array of inner radial fingers are used to displace the points to lie horizontally flat in one axial direction when the fingers and pushed in the opposite axial direction. With the barbs or points displaced to lie horizontally flat, the flexible ring tack can be loaded on a catheter delivery tube and held down by a cover. The fingers are then removed so that they are not present to obscure the blood vessel when the tack is installed. At the desired position, the retainer cover is displaced to release the ring tack which springs up to extend its points radially outwardly for embedding into the plaque. The body of the annular ring may have differing degrees of thickness and different designs for the fingers in the central area, such as the raised triangular anchors 59 and radial fingers 50 shown in FIG. 5.

FIGS. 7A-7D show alternative shapes for the third embodiment of FIG. 5 with a variety of different anchoring designs 72, 73, 78, 80. The fingers 76, 77 for bending the points flat for insertion are included with any of the designs. When the fingers are removed after pre-loading, and the flexible ring tack has been deployed, the inner area 74, 75 within the annular ring 79, 82 is left unobstructed.

Figure 6:
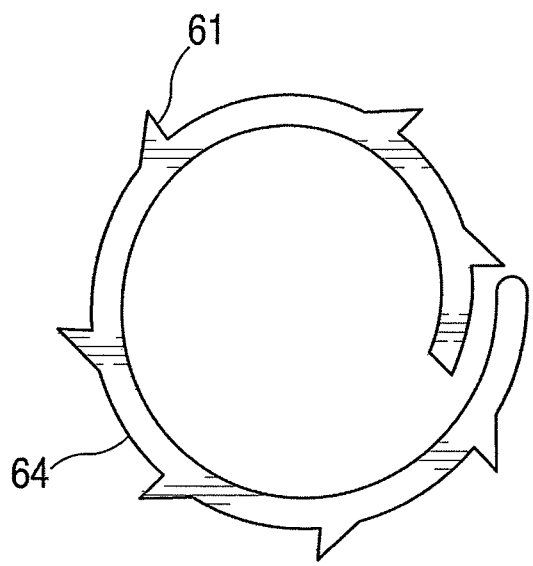
FIG. 6 is a schematic diagram of another embodiment of a spiral coil tack with unjoined ends that can be pulled in opposite directions horizontally to reduce its cross-sectional diameter for insertion in the blood vessel.
Figure 7A:
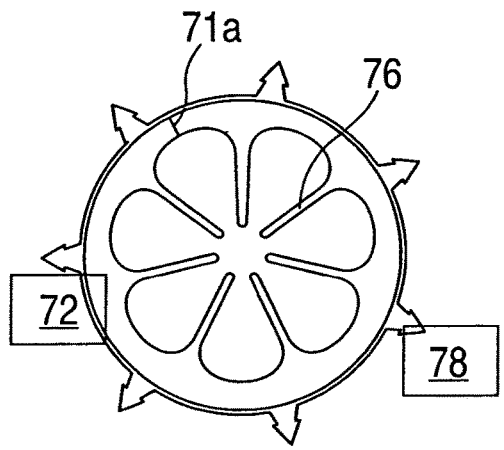
FIGS. 7A-7D show alternative shapes for the flexing star tack of FIG. 5 with a variety of different elevating element designs.
Figure 7B:
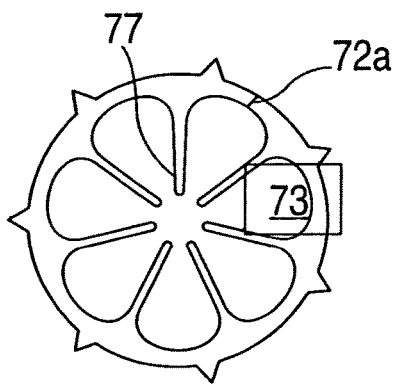
Figure 7C:
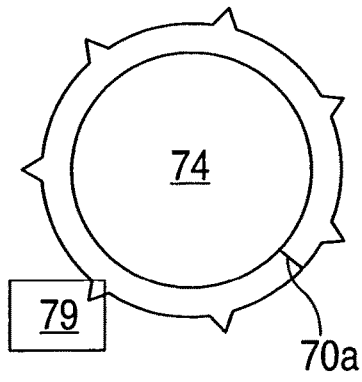
Figure 7D:
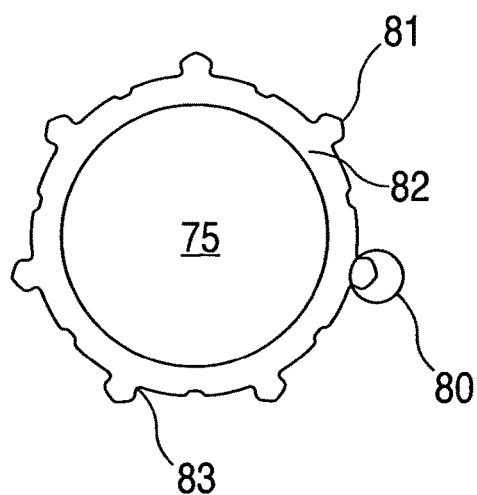

Referring to FIG. 6, a fourth preferred embodiment of the previous plaque tack device is formed in a coil shape 64 with ends unjoined and with barbs or points 61 on its outer periphery. The ends are pulled longitudinally in opposite directions to flatten the annular band to a spiral shape extending linearly so that it can be carried around or inside the length of a tubular sheath into the blood vessel held in place by a retainer element. At the desired position in the blood vessel, the retainer element is released to allow the tack to expand back to its full-diameter annular shape against the plaque.

Figure 14:
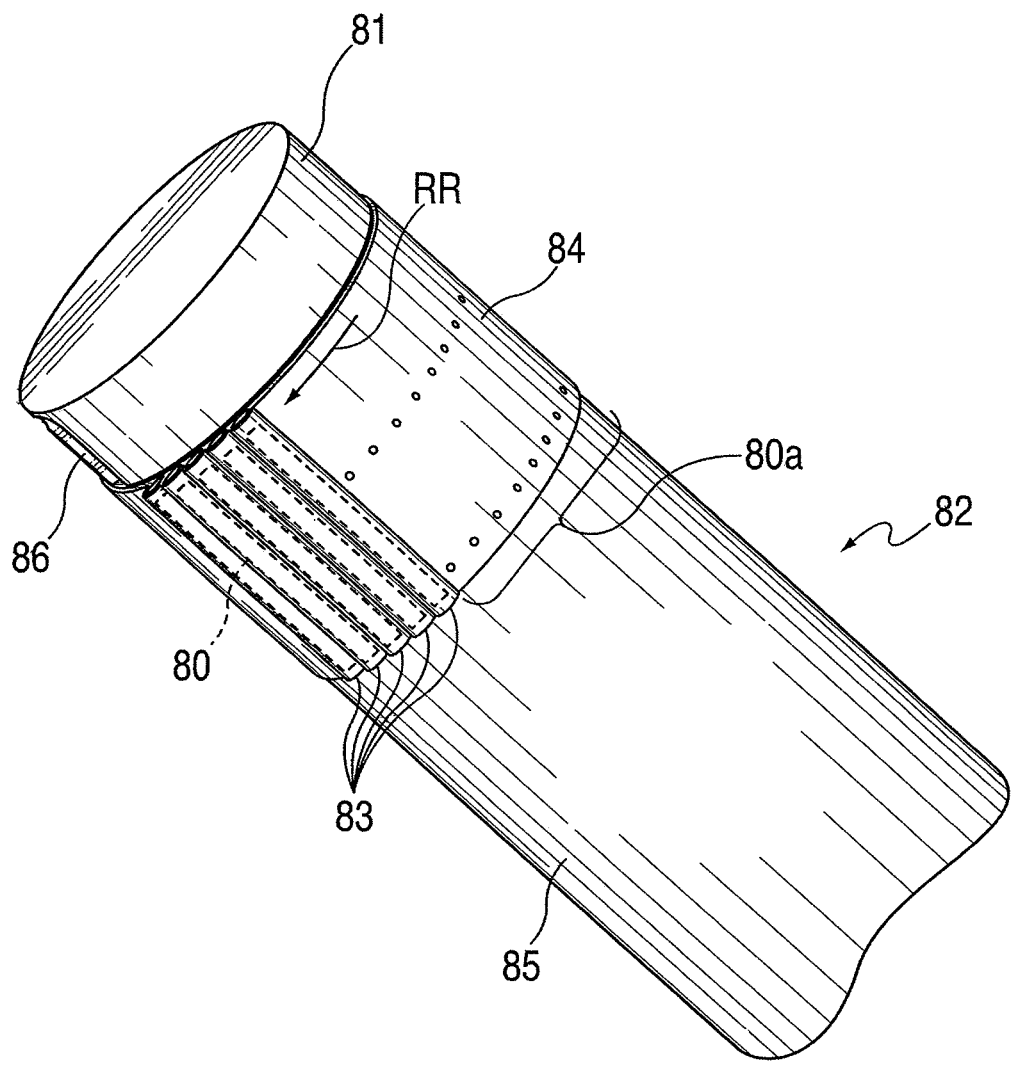
FIG. 14 is a schematic representation of the ribbon tack loaded in multiple units on the delivery head of a catheter tube for insertion into the blood vessel.
Figure 15:
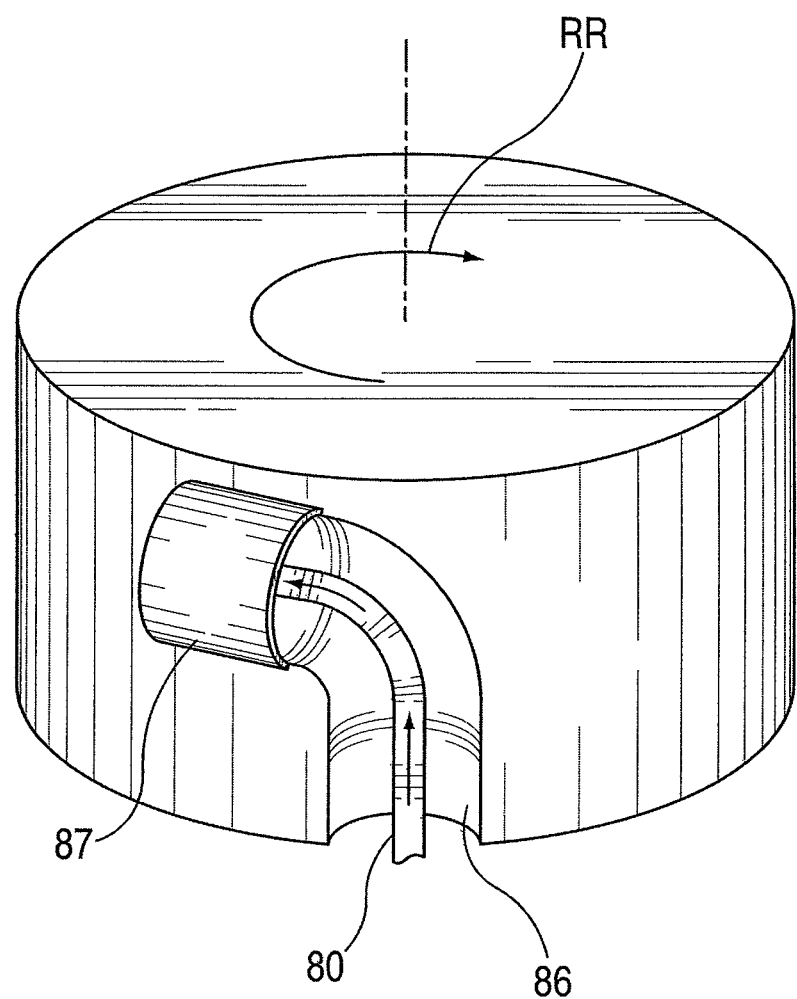
FIG. 15 is a detailed view of the delivery head for the ribbon tacks in FIG. 14.

FIGS. 14 and 15 show a preferred delivery method for the ribbon tack described above. Multiple flat ribbon strips 80 in linear form are arranged in parallel in an array 80a carried on the outer surface of the delivery head 81 of a tubular catheter 82. Each ribbon strip 80 is carried in a respective barrel 83 of a multi-barreled tack magazine 84 which wraps around the catheter, as indicated in FIG. 14. The catheter has an internal pressure chamber 85 which is loaded with saline solution or CO2 gas used to eject a ribbon strip from its barrel as it is moved by rotation of the magazine 84 in the direction RR to bring each ribbon strip in turn to an ejector position (left side of the figure) in alignment with an ejector track 86 formed in the delivery head. Pressurized fluid from the pressure chamber 85 is used to push a mover member that ejects the ribbon strip from its barrel into the ejector track 86. As shown in more detail in FIG. 15, the ejector track 86 leads into a curved outlet tunnel 87 which bends the ribbon strip towards its annular shape as the delivery head rotates. The outlet tunnel 87 curves 90 degrees from the axial direction of the catheter to the radial direction facing toward the vessel walls. This curved tunnel captures the end of the ribbon pushed into the ejector track and causes the middle part of the ribbon strip to bulge outward toward the blood vessel wall where it will lay down perpendicular to the axis of the blood vessel. The delivery head of the catheter rotates as part of the delivery mechanism. As the ribbon is being pushed out of the delivery head under hydraulic or propulsive pressure, the rotation of the delivery head allows the ribbon to be laid down in its annular shape spanning the blood vessel walls.

Figure 16:
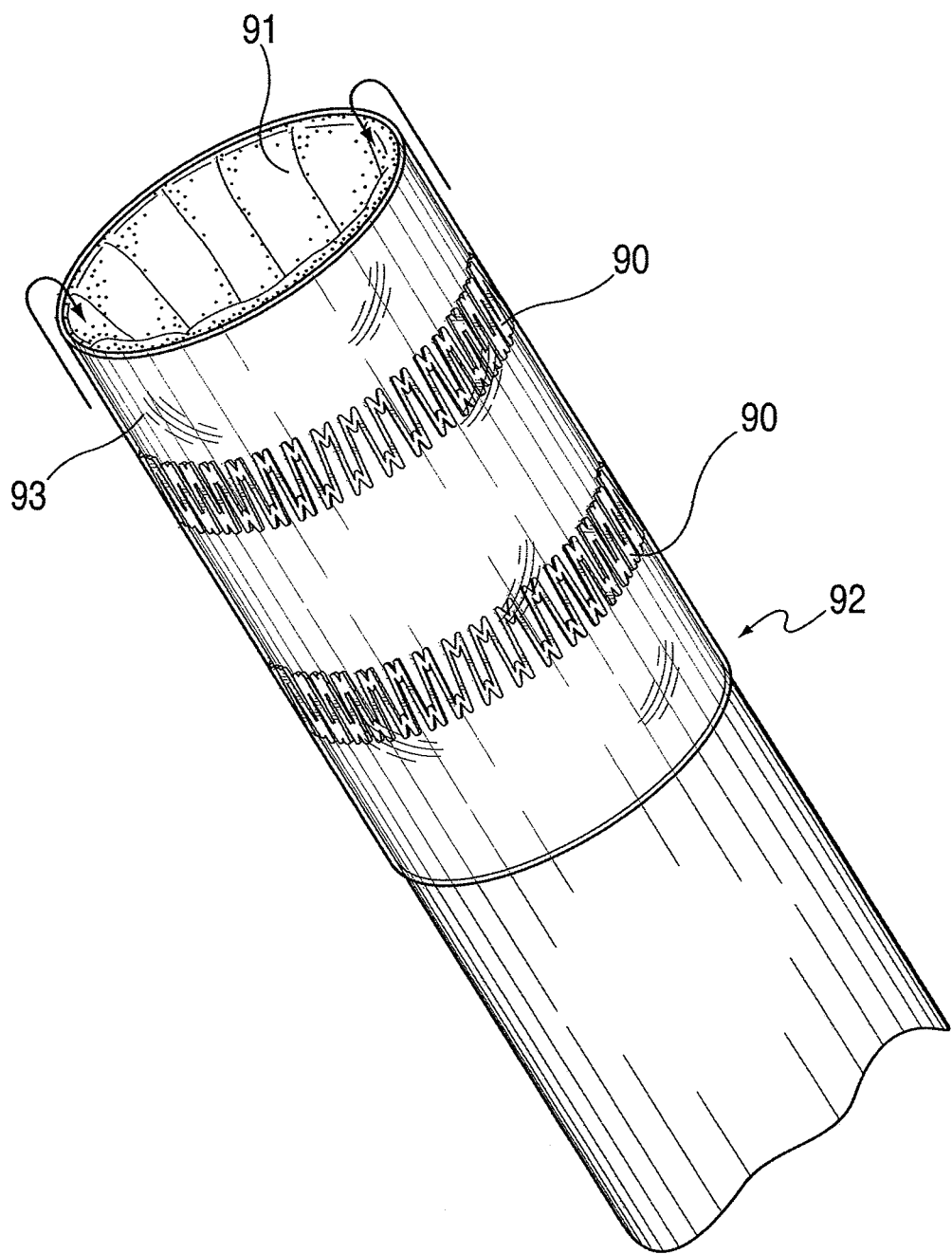
FIG. 16 is a schematic representation of the folding ring tack loaded in multiple units on the delivery head of a catheter tube with a retainer for holding them on the sheath in compressed form.
Figure 17:
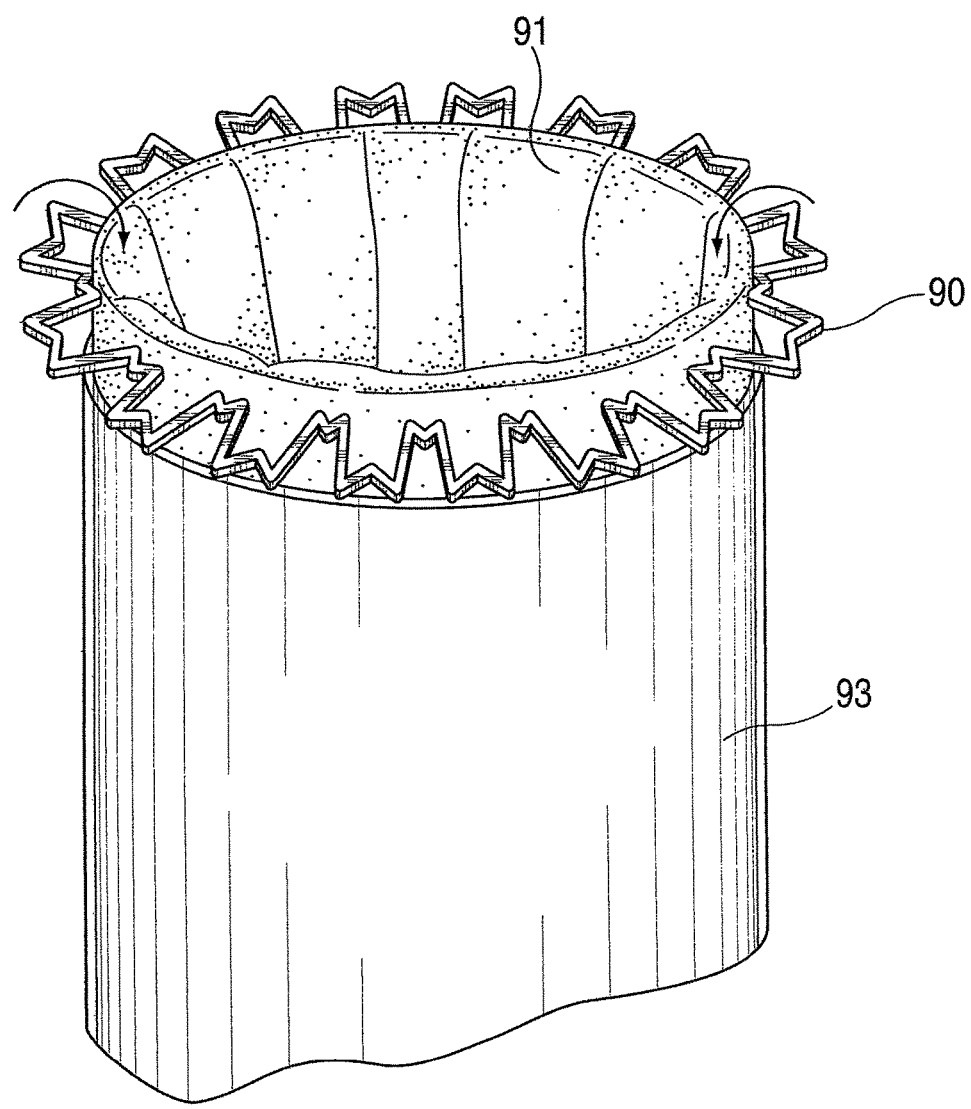
FIG. 17 is a schematic representation showing the folding ring tack partially deployed.
Figure 18:
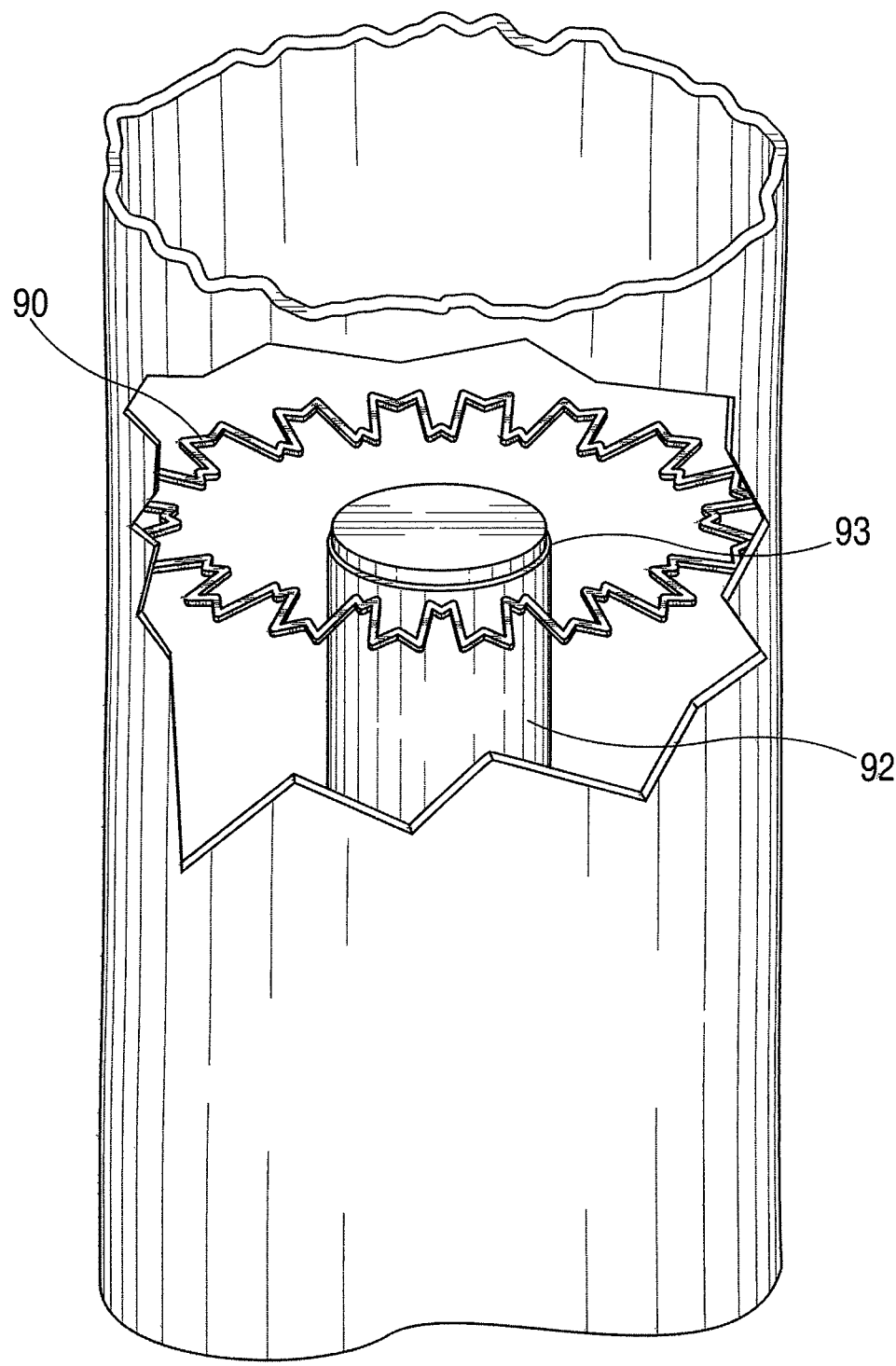
FIG. 18 is a schematic representation showing folding ring tack fully deployed in the blood vessel.

A preferred delivery method for the second described embodiment of the folding ring tack of FIG. 13 is shown in FIGS. 16, 17, and 18. The folding ring tack has an overall circular shape with inner V bends that allow it to be folded in zig-zag fashion to a compressed smaller-volume form for loading onto the delivery end of a catheter tube 92. As shown in FIG. 16, multiple units of the compressed folding ring tacks 90 are arrayed in a series on the surface of the tube. The catheter tube is hollow and lined with a fabric 91 that slides over the outer surface of the tube and is pulled over the end of the tube into its interior (direction of the U-shaped arrows). The fabric is made of a strong, durable material with low friction such as Teflon or Kevlar or like material. Multiple tacks may be loaded onto the surface of the fabric covering the outer surface of the catheter tube. The tacks are held down in their compressed, folded form by a shell or cover 93 that is telescoped over the catheter tube and prevents early deployment of the tacks. The shell may be a transparent plastic sleeve or similar structure having its end set back a small distance from the end of the catheter tube. As the fabric 91 is pulled inside the tube is pulled, the compressed tack 90 is advanced toward the end of the catheter tube. When the tack reaches the end, it is released from the shell 93, and springs back to its original shape of an annular band with outer barbs the embed or are emplaced against the plaque and blood vessel walls. FIG. 17 shows this process in action with the tack half-way deployed. The fabric 91 advancing the tack 90 is being pulled into the center of the hollow delivery tube. FIG. 18 shows the tack in place in the blood vessel after it has been separated from the delivery catheter.

The third preferred embodiment of the flexing ring tack of FIG. 5 may be deployed by a similar method as described above, by loading onto a similar sliding fabric carrier which is pulled over the outer surface of a catheter tube, with a shell sleeved over the tube for retaining the tacks from deployment until each reaches the end of the tube.

Figure 19A:
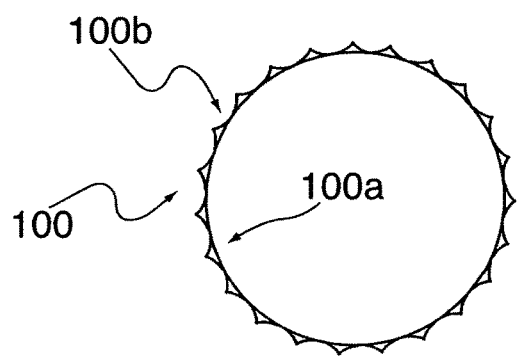
FIG. 19A shows a fifth embodiment of a metallic mesh tack in end view.
Figure 19B:
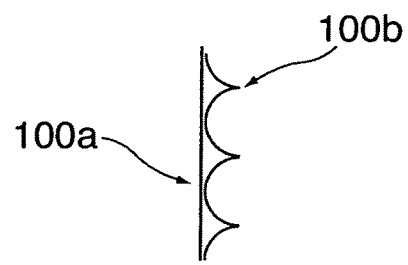
FIG. 19B shows it in side view.
Figure 19C:
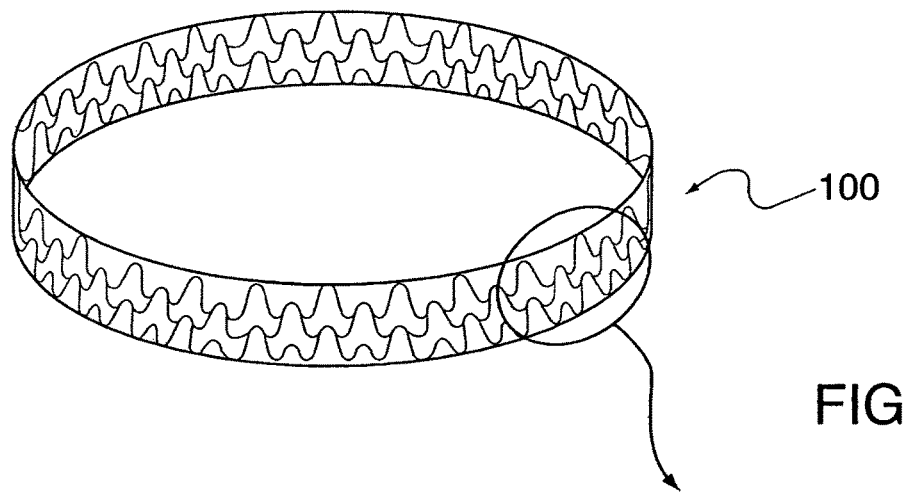
FIG. 19C shows the metallic mesh tack in perspective.
Figure 19D:
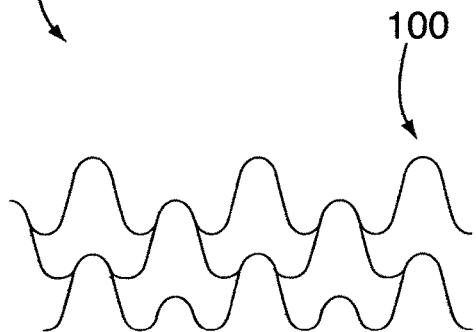
FIG. 19D shows a section of the metallic mesh tack in a detailed view.
Figure 20:
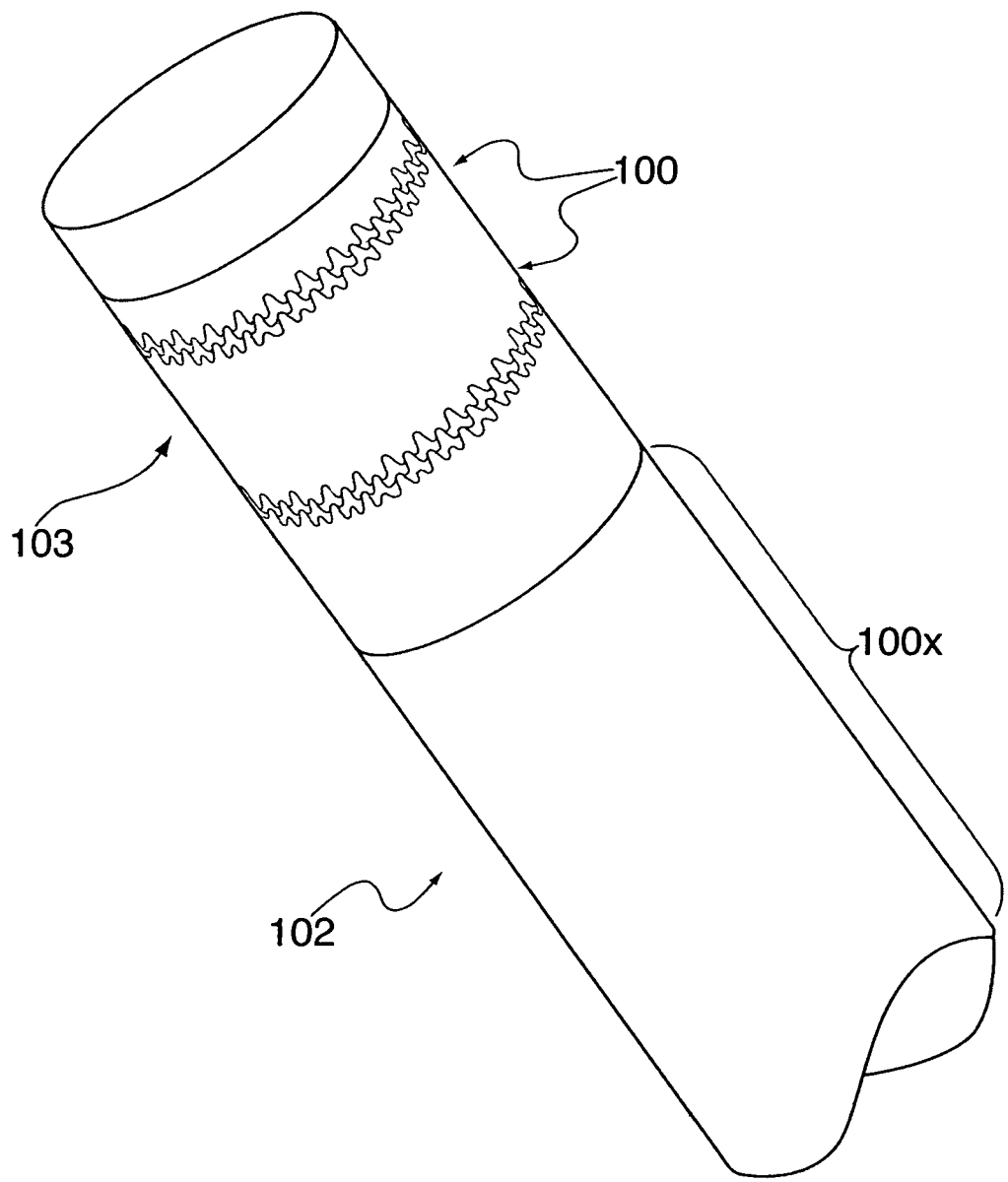
FIG. 20 is a schematic representation showing multiple units of the metallic mesh tack loaded on a catheter delivery tube.
Figure 21:
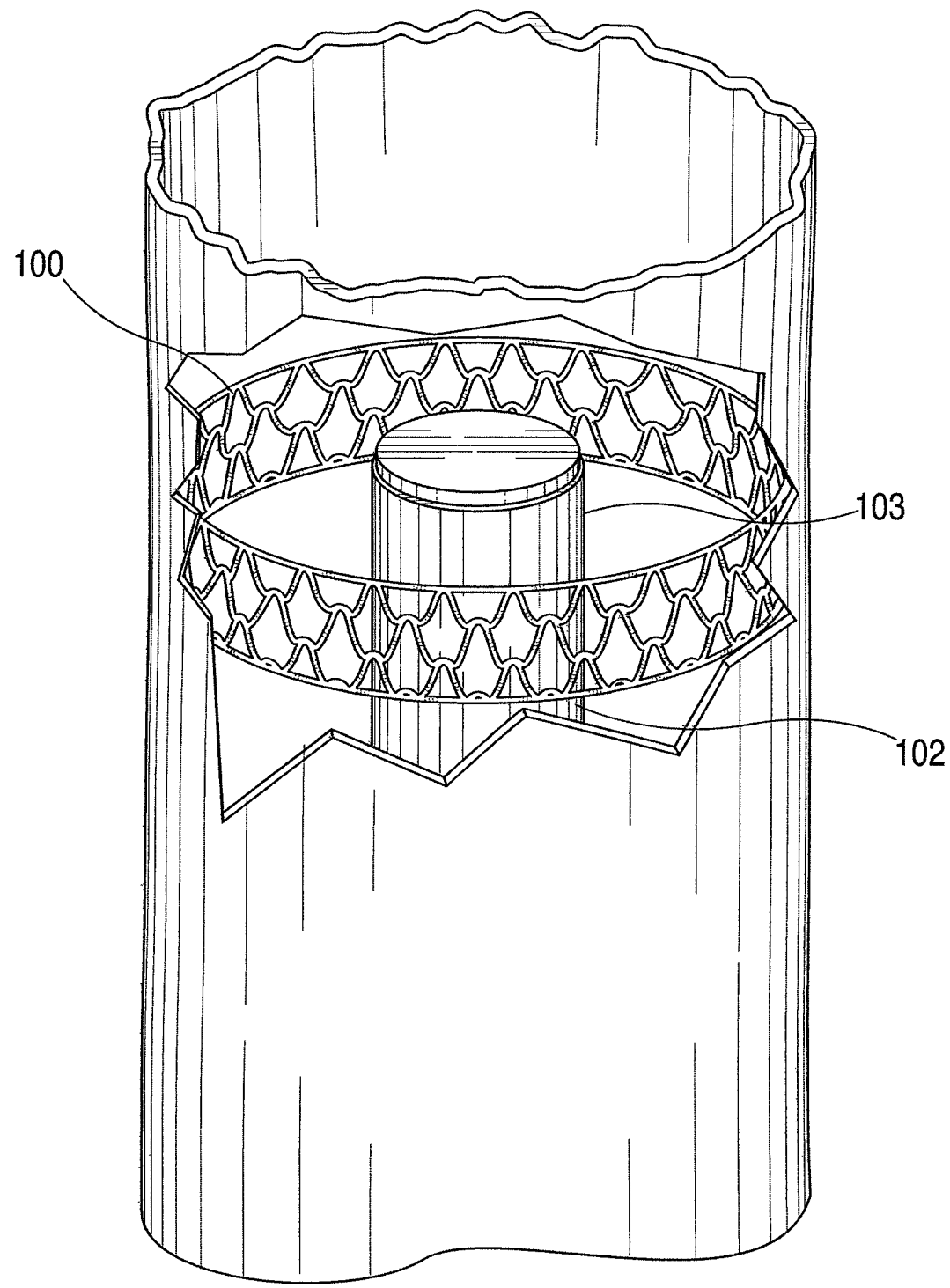
FIG. 21 is a schematic representation showing the metallic mesh tack released from the delivery head and fully expanded in the blood vessel.

A fifth embodiment of the previous plaque tack in the form of a metallic mesh tack is illustrated in FIGS. 19A-D, and its manner of deployment in FIGS. 20 and 21. In FIG. 19A, the metallic mesh tack is shown in end view having an annular band 100a formed of interleaved mesh, and outer points or barbs 100b. The metallic mesh tack may be laser cut or etched out of a metal tube form or made of thin metal wire which is looped and interleaved in a mesh that is welded, soldered, looped and/or linked together into the desired mesh shape. FIG. 19B shows the metallic mesh tack in side view with barbs projecting from the annular band 100a. The barbs on its outward surface will contact and embed into the wall of the blood vessel. FIG. 19C shows the metallic mesh tack at rest in its fully expanded state in perspective view, and FIG. 19D shows a section of the metallic mesh tack in a detailed view. The mesh pattern is specifically designed so that it can be compressed radially inward to a smaller-volume size for loading on a catheter delivery device to be inserted into the blood vessel.

A preferred method of delivery for the metallic mesh tack is shown in FIG. 20. Multiple mesh tacks 100 are compressed to its smaller-volume size and loaded onto the surface of a catheter delivery tube 102 in an array 100x over a given length of the tube. As in the previously described delivery method, a cover or shell 103 is sleeved over the surface of the tube to hold the tacks in their compressed state and prevent early deployment of the tacks. As the cover 103 is withdrawn down the length of the tube, each mesh tack in turn is released and expands to its full-volume size. FIG. 21 shows the mesh tack 100 expanded and deployed in the blood vessel.

Figure 22:
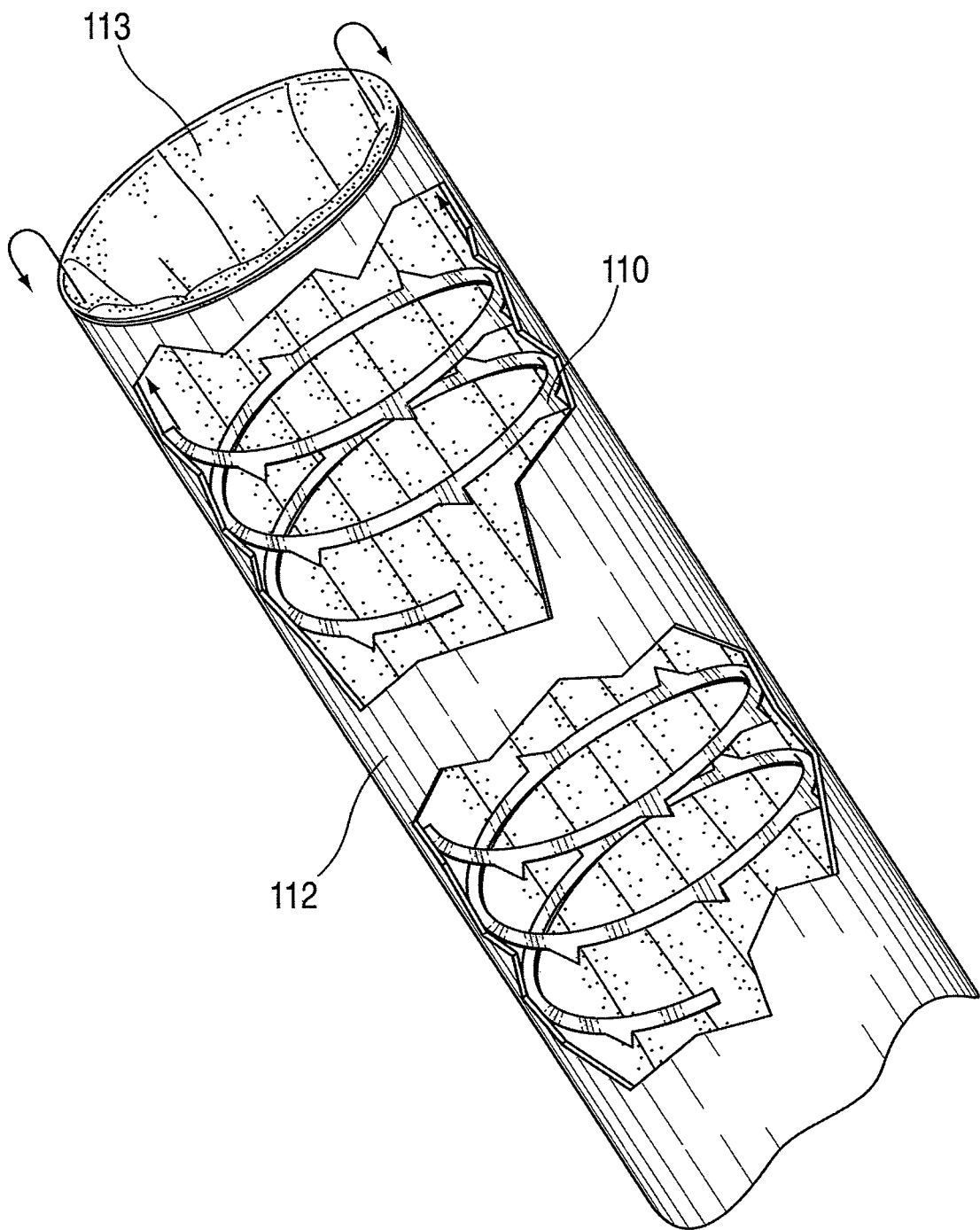
FIG. 22 is a schematic representation the spiral coil tack loaded in multiple units on the delivery head of a sheath and held down by a retainer cover.
Figure 23:
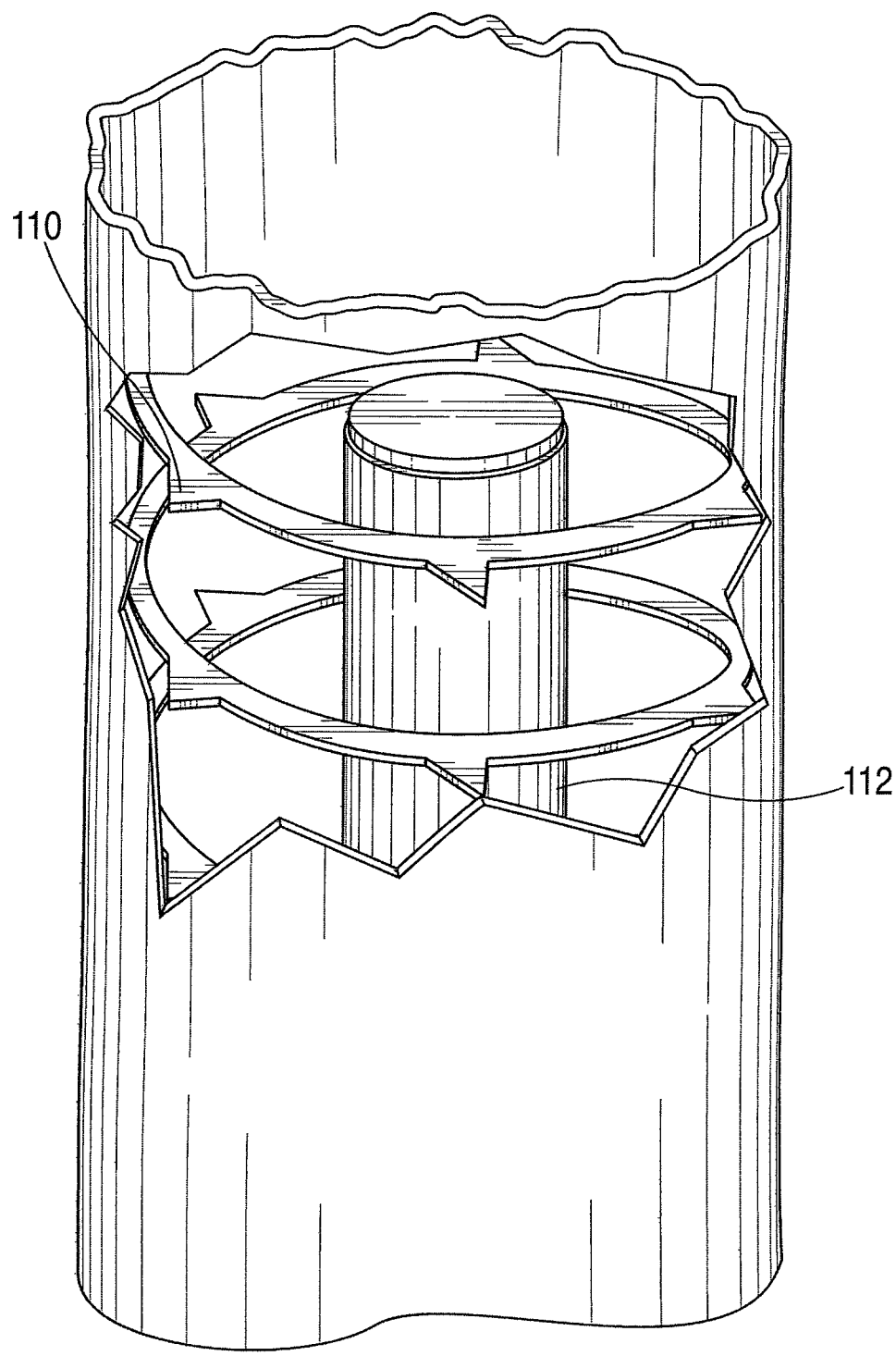
FIG. 23 is a schematic representation showing the spiral coil tack released from the delivery head and fully expanded in the blood vessel.

A preferred delivery method for the fourth described embodiment of the spiral coil tack of FIG. 6 is illustrated in FIGS. 22 and 23. The coil shaped tack in FIG. 6 is formed with barbs and a band with unjoined ends that may or may not have a taper with a varying degrees of thickness along its length. This design is uncoiled in its rest state and looks like a "broken" circle. The coil tack can be compressed to a fraction of its at-rest diameter by pulling its ends in opposite linear directions to form a tight spiral that occupies a smaller-diameter volume so that it can be inserted into the blood vessel. When released it can expand to several times the diameter of its spiral form. FIG. 22 shows multiple units of spiral coil tacks 110 loaded in the interior of the catheter delivery tube 112. When the tack is compressed, it occupies several spiral turns and it spaced out longitudinally. In this case, the delivery catheter is lined with fabric 113 slidable on its interior surface over the end of the tube to its outside (indicated by the pair of U-shaped arrows). As the fabric is pulled through the center of the tube, the tack is advanced toward the end of the delivery catheter. When the tack reaches the end of the delivery catheter, the tack is released from the tube and re-expands to its full size to be deployed into the wall of the blood vessel. FIG. 23 shows the tack deployed in the blood vessel.

In the previous embodiments described above, the preferred plaque tack device may be made from Nitinol, silicon composite (with or without an inert coating), polyglycolic acid, or some other superelastic material. The anchors can have a preferred penetration length of 0.01 mm to 5 mm. The strip of material can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. It may be fabricated from metal, plastic, ceramic, or composite material.

The plaque tack device is designed to be inherently self-aligning, i.e., its mechanical installation can accommodate small misalignments. By reducing stress in the strut members while gripping the arterial wall in the center of the design, the tack self aligns with the arterial longitudinal axis. Design features that offer stress relief and provide uniform distribution of the unfolding struts include narrow spacing of the barbs, non-uniformly thick struts, and barbs heads that are angled to reduce device from springing forward during delivery. Circumferentially oriented barbs located at each bridge member offer gripping force with the catheter tip and embedding features when lying on the artery wall. These design features serve to facilitate placing the tacks in specific locations within diseased blood vessels. With respect to the piercing barb that has a pointed shape, it can be used to embed in objects having irregular surfaces such as plaque or dissected or damaged artery surfaces. After deployment of the plaque tack, the surgeon has the option of placing an angioplasty balloon at the site of the tack and inflating the balloon to press the anchor or anchors into the wall of the blood vessel.

Plaque Tack Design Parameters

The purposes of the plaque tack described herein, as distinct from traditional stenting, are to reduce the amount of implanted foreign material to a minimum while still performing focal treatment of the blood vessel condition so as to cause a minimum of blood vessel wall reaction and adverse post-treatment re-stenosis. The preferred plaque tack is designed to have substantially less metal coverage and/or contact with the blood vessel surface, thereby inciting less acute and chronic inflammation. Reduced pressure of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions. The plaque tack is deployed only where needed to tack down plaque that has been disrupted by balloon angioplasty or other mechanisms. Rather than cover an entire area of treatment, the plaque tack is placed locally and selectively, and not extending into normal or less diseased artery segments. This permits the blood vessel to retain its natural flexibility because there is a minimal to no scaffolding effect when a small profile tack is used locally or when even multiple tacks are spaced apart over the area of treatment. Reduction in the pressure profile is achieved by using "points-of-contact" to achieve higher pressure at focal points and lifting neighboring strut section away from blood vessel wall to reduce the overall load of the outward pressure elsewhere on the tack strut structure.

One parameter for design of a plaque tack is having a tack length to diameter (L/D) ratio about equal to or less than 1. That is, the length of the tack along the axis of the blood vessel is about equal to or less than the diameter of the tack. The preferred plaque tack is thus shaped like an annular ring or band, whereas the typical stent is shaped like an elongated tube. The small-profile tack can thus be used locally for targeted treatment of disrupted regions of the blood vessel surface with a minimum of foreign material coverage or contact. Our tests show that a plaque tack with length/diameter ratio ≤1 causes almost no biological reaction or subsequent blood vessel narrowing in comparison to a traditional stent where the length is greater than the diameter, and usually much greater. Our tests indicate that device L/D≤1 results in a reduction in scaffolding much less than that of the typical stent and causes less arterial wall reaction. For application at sites of small dissection after balloon angioplasty, a plaque tack of minimal footprint may be used such as a single, thin ring-type tack with an L/D ratio in the range of 1/10 to 1/100.

Studies on stenting have shown that the length of a stent is correlated with a tendency for occlusion in multiple vascular territories. The more stent length that has been placed, the higher likelihood that the reconstruction will fail. The length of a stent is also directly linked to the frequency and tendency of the stent to break when placed in the superficial femoral artery. The medical literature indicates that the superficial femoral artery performs like a rubber band, and it is likely that changes to the natural elongation and contraction of the superficial femoral artery play a significant role in the failure mode of superficial femoral artery stents. In contrast, the small-profile plaque tack can be implanted only in local areas requiring their use, thereby enabling the blood vessel to retain its natural flexibility to move and bend even after the surface has undergone tacking. Multiple tacks may be implanted separated by regions free of metallic support, thereby leaving the artery free to bend more naturally.

Outward radial pressure exerted on the blood vessel wall can also be substantially reduced by the small-profile tack design, even when multiple tacks are used in a spaced-apart configuration. To minimize this outward force while still providing the required retention of dissections against the arterial wall, a series of anchor barbs is utilized. The presence of the barbs applying focal pressure to the wall of the artery allows the rest of the tack to apply minimum outward force to the artery wall. The points of the barbs which apply the pressure are very focal, and this is where the most force is applied. The focal nature of the application of the pressure exerted by the tack also minimizes the structural effects of the device. The uniformly distributed focal elevating elements provide a distribution of radial energy maximizing the tendency to form a circular lumen.

Another important parameter for design of a plaque tack is the ratio of Vessel Coverage Area (C) to Total Vessel Surface area (TVS). This equation can be applied to one tack device or when several spaced-apart tack devices are placed across the length of a blood vessel treatment area. For a plaque tack, the C/TVS ratio is in the range of about 60% or less, whereas for a stent it can be 100% or more (if applied to overlap the treatment site). For a focal lesion, the conventional treated vessel length is X+10 mm to 20 mm where X is the length of the lesion and the added length is adjoining on normal or less diseased artery proximal or distal to the lesion. In traditional stenting, the entire treated vessel length would be covered with a stent. For example, in the case of a 2 cm lesion, the treated vessel length would be 3 to 4 cm (usually a single stent of this length would be selected), so that C/TVS is 150%-200%. In contrast, with tack placement, about ½ of X would be covered, and none of the adjoining normal or less diseased artery would be treated. For example, in a 2 cm lesion, approximately 1 cm would be covered, so that the C/TVS ratio is about 60% or less. The key to this innovative approach is placement of bands only in regions of dissections requiring arterial tacking.

Figure 25:
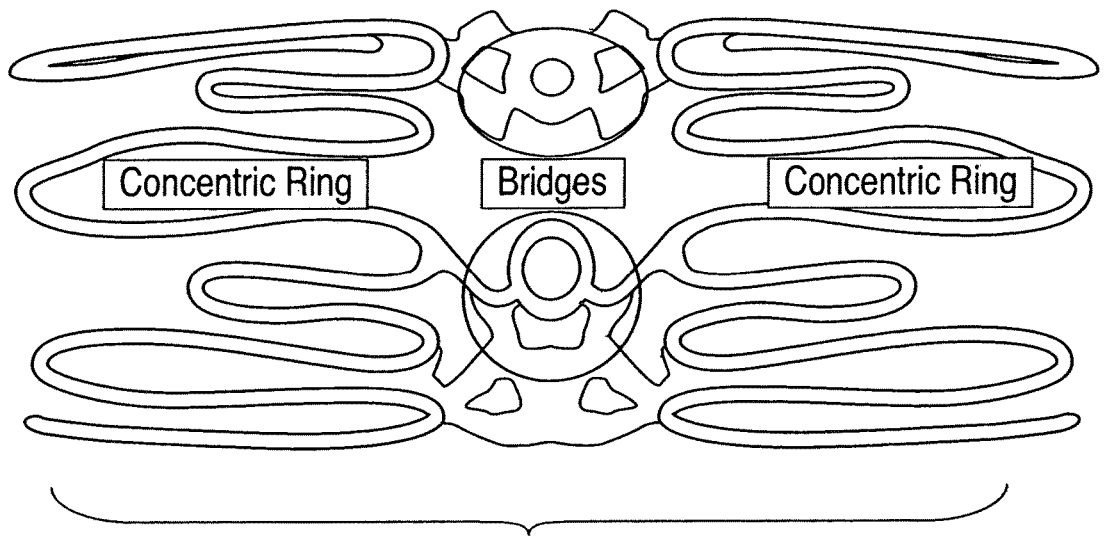
FIG. 25 shows a detailed view of another embodiment of the plaque tack formed with concentric rings connected by a series of bridging members.

In another preferred embodiment, a tack device is formed with concentric side rings or mesh bands connected by longitudinal bridge members. FIG. 25 shows a detailed view of the preferred embodiment of the plaque tack formed with concentric rings on each side connected by a series of bridging members. In the figure the concentric side rings are shown compressed for delivery in the blood vessel. When expanded, the diameter of the tack device is about equal to the width of the tack device. This embodiment can be laser cut from tube or tapered tube stock, where the tapered tube enables simplified production of tack devices with focal elevating elements. The number of bridging members is chosen depending upon the application. For example, 6 or fewer bridge members may be used between the two concentric rings when desired for limiting neointimal hyperplasia.

The literature in the industry has noted that an important factor in stent design may be the ratio of Relative Metal Surface Area (RMS) compared to the number of longitudinal segments in the device structure, for example, as presented by Mosseri M, Rozenman Y, Mereuta A, Hasin Y, Gotsman M., "New Indicator for Stent Covering Area", in *Catheterization and Cardiovascular Diagnosis*, 1998, v. 445, pp. 188-192. As adapted from the RMS measure, an equation for Effective Metallic Interface (EMI) may be used to compare the embodiment of the tack device with longitudinal bridging members to a typical stent, as follows:

$$EMI = \frac{(1+n^2)C}{\sum_{s=1}^{x}(lw)_s}$$

Becomes:

$$EMI_F = \frac{C(1+(n-n_F)^2)}{\sum_{S=1}^{x}(lw - l_F w_F)_S}$$

where x is the number of sections of metal, l is an individual metal section length, w is an individual metal section width, C is the vessel coverage area underneath the device (lumen surface), and n is the number of bridge members longitudinally connected between circumferentially oriented segments. The inclusion of metal sections that are floating (floating length $l_F$, floating width $W_F$, and number of floating bridges $n_F$,) reduces the EMI further which is captured mathematically as a summation with negative variables in the $EMI_F$ equation. The summation found in the denominator can be interpreted as the total metal surface area. The embodiment of the tack device with longitudinal bridging members has an EMI≤10, whereas the EMI of a typical stent would be several times greater. This low EMI is due to the nature of the tack design having a small foot-print and minimal longitudinal bridges while a stent typically has a large foot-print and would be a multiple several times that.

Figure 26:
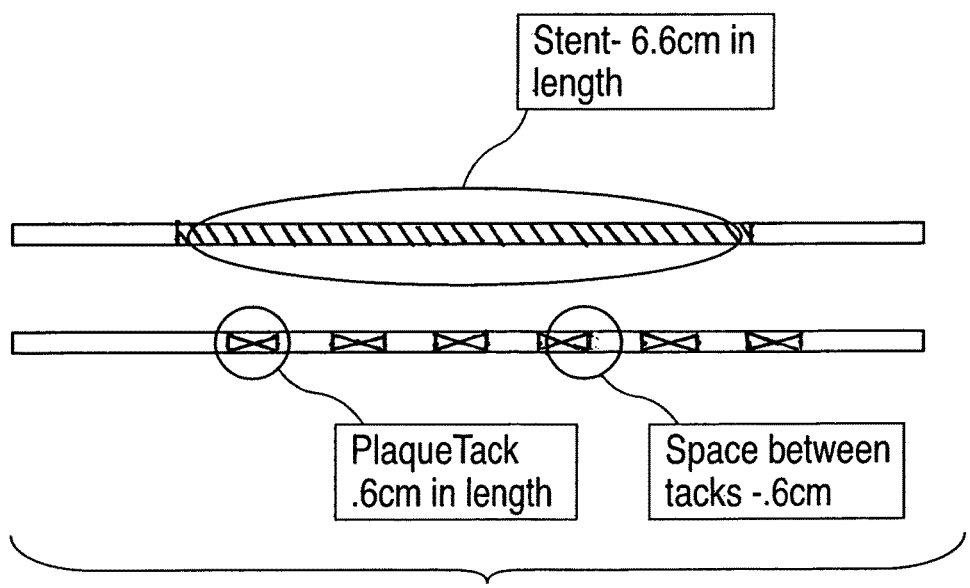
FIG. 26 illustrates the use of multiple tack devices which are spaced apart over the length of a treatment site as compared to a typical stent.

FIG. 26 illustrates the use of multiple tack devices which are spaced apart over the length as compared to a treatment site compared to a typical stent. Preferably, the spacing between tack devices is at least the width of the tack device. Note that the spacing between adjacent tack devices leaves untreated vessel area. A typical stent is shown in the upper part of the figure compared to the use of 6 spaced-apart tack devices at the bottom part of the figure. The overall length of treatment area is 6.6 cm (the same length of the stent) while each band is shown as 6 mm long separated by 6 mm spaces. Therefore, the Vessel Coverage Area for the stent is the same as Total Vessel Surface area (=6.6 cm×0.6π, or 12.44 cm$^2$) which gives a C/TVS ratio of 100%. For the series of spaced-apart tack devices, C is equal to 6×0.6 cm×0.6π, or 6.78 cm$^2$, while TVS is 12.44 cm$^2$, therefore the C/TVS ratio is equal to 54.5%.

When two or more stents need to be employed over an extended length of treatment site, it has been a conventional practice to overlap adjoining stents to prevent kinking between stents. Due to the increased metal lattice, the region of overlap becomes highly rigid and noncompliant. This noncompliance limits the natural arterial flexibility and increases the tendency for restenosis. Stent fractures occur more frequently in the superficial femoral artery where this bending has a high frequency and are common when multiple stents are deployed and overlap. Stent fractures are associated with a higher risk of in-stent restenosis and re-occlusion. In contrast, the plaque tacks are designed to be applied in local areas and not to be overlapped. Optimal spacing is a minimum of 1 tack width apart for tacks. This permits the artery to maintain its flexibility, and only a half or less of the treated length of the artery will be covered with metal.

The presence of the plaque tack outer barbs minimizes the pressure of the overall structure upon the blood vessel wall by transferring regional outward forces to focal pressure points, thereby applying a higher pressure at the focal points and low pressure through the barb contact with the wall. The presence of the barbs applying focal pressure to the wall of the artery allows the rest of the tack to apply minimum outward force to the artery wall. Wherever the barbs are placed, the outward radial energy is maximized at that region, producing a slight outward bowing of the arterial wall. The outward bowing can be used for arterial shaping or molding, for example, 5 or more uniformly distributed focal points can be used to form a circulate lumen. Circular lumens offer additional benefit from the standpoint of the vessel wall interaction, independent of the vascular injury.

Use of Plaque Tack after Drug Eluting Balloon Angioplasty

The use of plaque tack devices can be combined with use of Drug Eluting Balloon (DEB) angioplasty to manage post angioplasty dissection and avoid the need for stents. In DEB angioplasty, a drug-eluting balloon or a drug coated balloon is prepared in a conventional manner. The drug may be one, or a combination, of biologically active agents that are used for various functions, such as anti-thrombotic, anti-mitotic, anti-proliferative, anti-inflammatory, stimulative of healing, or other functions. The DEB is delivered on a guidewire across an area of blockage or narrowing in the blood vessel system. The DEB is inflated to a specific pressure and for a period of time consistent with the manufactures guidelines of use for treatment purposes, as it pertains the drug coating and the intended outcomes, then the DEB is deflated and removed. At this stage the medication from the DEB has been transferred to the wall of the blood vessel. Intravascular imaging by ultrasound is then used to assess the integrity of the artery and the smoothness of the blood vessel surface at the site where the balloon was inflated. The presence of damage along the surface may be indicated as dissection, elevation of plaque, disruption of tissue, irregularity of surface. The plaque tack is used to tack down the damaged, disrupted, dissected, or irregular blood vessel surface. This permits continuation of a 'stent-free' environment even if damage to the blood vessel has occurred as a result of balloon angioplasty.

At this stage the medication from the DEB has been transferred to the wall of the blood vessel. Contrast is administered into the blood vessel under fluoroscopic guidance or another method such as intravascular ultrasound is used to assess the integrity of the artery and the smoothness of the blood vessel surface at the site where the balloon was inflated. In some cases, one or more of these completion studies will demonstrate the presence of damage along the surface at the site of the balloon inflation. This damage may include dissection, elevation of plaque, disruption of tissue, irregularity of surface.

The plaque tack delivery catheter is loaded with multiple tacks that may be placed at the discretion of the operator, and advanced over a guidewire in the blood vessel to the location where the dissection or disruption or irregularity has occurred. The location is specifically and carefully identified using angiography. The plaque tack(s) is or are deployed at the location(s) of the lesion. More than one tack may be placed to tack down a major dissection. If more than one tack is placed, it may be placed only according to the rules of proper spacing of tacks. That is, the tack should be at least one tack-length apart and do not overlap. After placement of the tack, it may be further expanded into the wall of the blood vessel using a standard angioplasty balloon or a drug-eluting or drug coated balloon. The purpose of the tack is not to hold the blood vessel lumen open but to tack down the non-smooth or dissected surface of the blood vessel. This 'touch-up strategy' permits the resolution of the damage created by the drug-eluting or drug coated balloon without resorting to stent placement and thereby maintaining a 'stent-free' environment.

As a further measure, described above, the plaque tack device itself can be used to deliver medication to the blood vessel. In addition to the delivery of medication from the barbs, the tack can be coated with medication prior to tack placement. The purpose of this activity is to permit the tack to elute biologically active agent or agents that have positive effects on the blood vessel.

Improvement of Focal Elevating Elements

In the present invention disclosure, the plaque tack devices may be improved by expanding the use of barbs or focal elevating elements on the annular periphery of the device. The use of this new nomenclature is to distinguish the barbs as a feature with greater arterial wall penetration for use as anchors or stabilizers and are preferably placed on struts that connect ring elements, while focal elevating elements are features that may or may not penetrate but still offer regional strut elevation and are preferably placed at apexes of struts or periodically perpendicular to strut lengths. For both barbs and focal elevating elements the size of the interface between the tack and the arterial wall is preferably equal to or shorter than the strut width in at least one direction. The focal elevating elements are similar to barb elements but either do not penetrate or penetrate the tissue only slightly, thereby minimizing the amount of material surface area in contact with the plaque, and offer a set of relief sections for the outward pressure of the tack device adjacent to the focal elevating elements, thereby minimizing the friction generated at the blood vessel wall. The focal elevating elements are formed and configured on the annular periphery of the tack device in a similar manner as described for the previous tack device embodiments and include the addition of raised contact sections in addition to barbs or sharp points. The contact sections can provide improved tacking characteristics in that they increase the outward forces at the contact sections by compressing the plaque at the contact regions and decrease the outward force at the sections neighboring the focal elevating element. This offers regional pressure relief in some sections and increase pressure at the bumps or sharp points collectively offering a reduction in trauma and cellular response of the blood vessel wall.

Because the tack device is held in place by its own pressure exerted on the blood vessel surface, it is susceptible to friction, i.e., slight movement between the device and the vessel surface. Every time the organ moves (e.g., the leg during ambulation), the artery moves. It can be inferred that when the artery moves the working device sitting within the artery also moves but not necessarily every point of contact moves in synch with each other. Whenever there is even a small mismatch between the artery and the device the system rubs against each other promoting cellular reaction and device failure. It has been deduced from experimental data that this rubbing irritates the endothelium causing an inflammatory response. In the present invention, strategically placed focal elevating elements (FEEs) are implemented to reduce the overall regional friction load (thought to be a source of inflammation, cellular proliferation, and the healing response that leads to restenosis) of the area being held open. These raised sections produced by the FEEs limit the histological response of the tissue and the fatigue of the device by limiting the contact between the device and the tissue. Independent of the volume of contact, the tack devices smooth the lumen wall, and allow more natural vessel movement. It is this micro-movement that increases the cellular response of the blood vessel surface to the foreign device.

In configuration on the tack device, the focal elevating elements are designed to reduce effective metal interface (EMI) by minimizing the overall material contact with the blood vessel surface. The focal elevating element (FEE) is preferably configured as a narrow, lifted feature with enough height to penetrate the blood vessel and lift adjacent strut sections of the tack device off from contact with the arterial wall in order to reduce the surface area of foreign material in contact with the arterial wall. Reducing the contact burden is of particular value when the strut members are connecting circumferential rings or circumferentially oriented strut bands. Strut sections in contact with the blood vessel walls can produce microfriction when they move or rub against the blood vessel walls. By reducing the foreign material contact area against the blood vessel wall, the tendency for production of microfriction contact is reduced.

Figure 27:
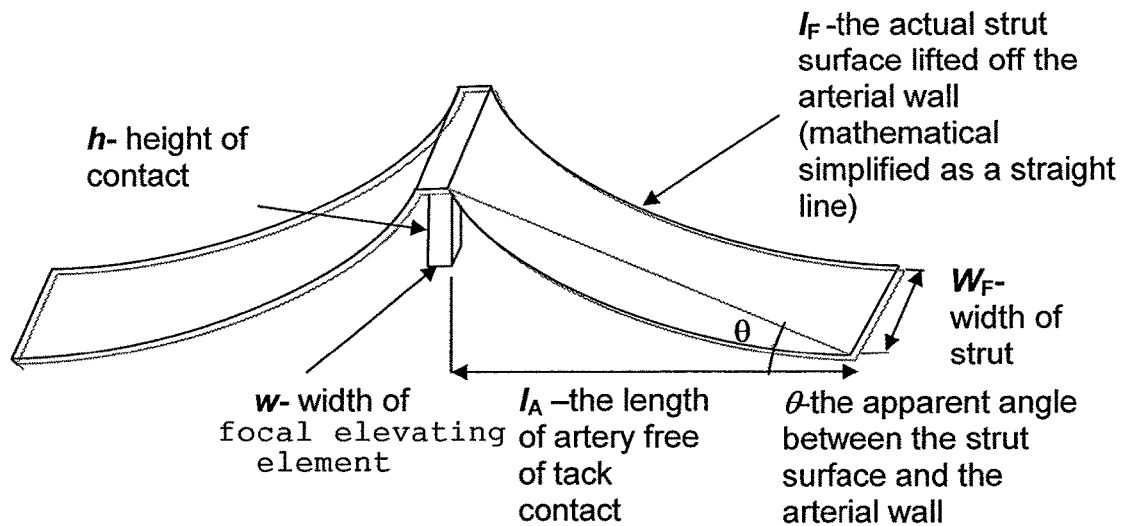
FIG. 27 is a schematic diagram illustrating the variables for computing the elevated tack surface due to the use of focal elevating elements in a plaque tack device.

Referring to FIG. 27, a schematic diagram illustrates the preferred design assumptions for the use of focal elevating elements on the plaque tack device. In the figure, h refers to the height of the focal elevating element that is extended out of the blood vessel (note: the penetration depth of the focal elevating element that is anchored into the artery or plaque body is not included in this calculation), w refers to the width of the focal elevating element (at its base), and $l_F$ refers to the adjacent strut surface lifted off the arterial wall (mathematically simplified as a straight line). The struts adjacent to the focal elevating element may be fabricated with shape memory materials or designed as a compression wave providing compensation for lumen diameter variations. The strut forces adjacent to the focal elevating elements produce an outward bowing of the struts produced by the forces of the struts wanting to expand until they are in contact with the blood vessel wall. $l_A$ refers to the length of arterial wall that is kept out of contact with any adjacent strut structure by the focal elevating element.

The focal elevating elements may be formed as cylindrical, rectangular, spherical, conical, tear dropped, pyramidal, or inclined elements on the annular periphery of the tack device. They can be formed by bending or stamping a section of the tack structure, by an additive process (such as by welding or annealing on a peripheral surface), by a subtractive process (such as by grinding or etching away surrounding material so that the bump element is higher than the surrounding surface, or by modifying small sections of the peripheral surface to be higher than the surrounding surface before or after sheet or tube cutting. For example, one method of modification of small sections of a mesh tack structure is by knotting, twisting, bending or weaving small sections of the wire mesh to produce raised elements from the mesh surface which are the interface with the artery wall of the tack devices.

Properly oriented and symmetrically positioned focal elevating elements can provide foci for expansion force. As the device exerts outward forces and the artery exerts inward forces, the focal elevating elements can be positioned at strategically located positions reducing the outward pressure of strut sections neighboring the focal elevating elements.

Both barbs and focal elevating elements offer strategic advantages that include: the reduction in pressure burden across the tack struts by reducing the contact area and translating the outward forces to the barbs and focal elevating elements, minimizing surface contact which offers a reduction in the tendency of frictional loading driven by micro movement between the arterial wall and the tack strut, and the stabilization of anchoring the tack where the barb or focal elevating element penetrates the vessel wall a fraction of the features height.

Figure 28:
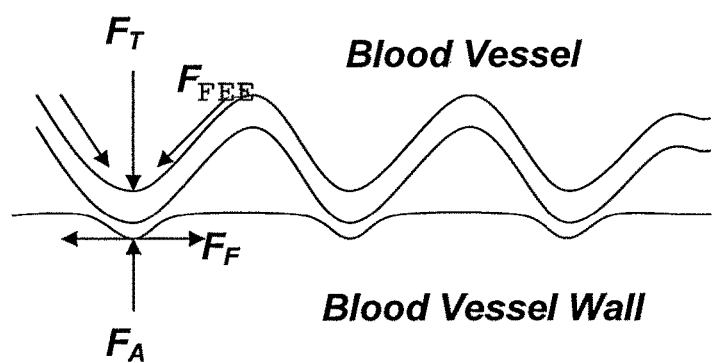
FIG. 28 illustrates use of a tack device with focal elevating elements for holding a plaque position to a blood vessel wall.

Because the tack device is held in place by its own outward force pressure exerted on the plaque and blood vessel surface, it may be susceptible to friction, i.e., slight movement between the device and the vessel surface. FIG. 28 illustrates the forces at play between the tack's focal elevating elements and the arterial wall. $F_T$ is the circumferential force exerted by the tack device against the arterial walls force, $F_A$. $F_{FEE}$ is an additive circumferential force at the focal elevating element generated by the design and material choice and $F_F$ is the frictional force of the artery generated when the artery changes its orientation or shape due to body forces. Every time a body party moves, the blood vessels move slightly as well. The focal elevating elements can be strategically positioned to reduce local friction loading which may cause inflammation, cellular proliferation, or bodily response that leads to restenosis.

The number and locations of focal elevating elements can affect the overall Relative Metal Surface Area (RMS) which was explained previously. The focal elevating elements may be positioned along the lengths of the tack device surfaces such that a minimal amount of metal surface area is in contact with the artery wall. Focal elevating elements placed at bridges between circumferential strut rings or at the apexes of strut sections of the tack device can offer a majority of arterial injury relief. When focal elevating elements are placed only at apexes and bridges, the RMS of the strut members making up the concentric ring changes a little while the RMS of the bridges is reduced more significantly, due to the narrow length, offering relief of relative motion of the circumferentially oriented strut rings.

Figure 29A:
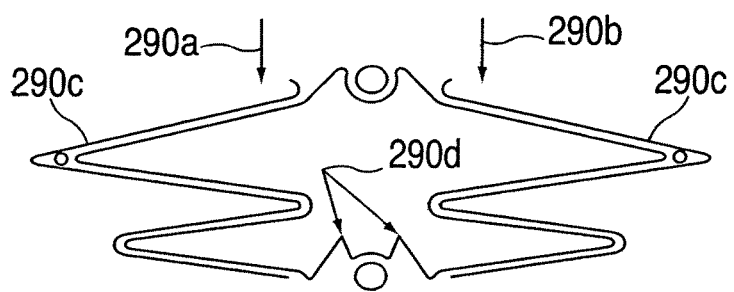
Figure 29B:
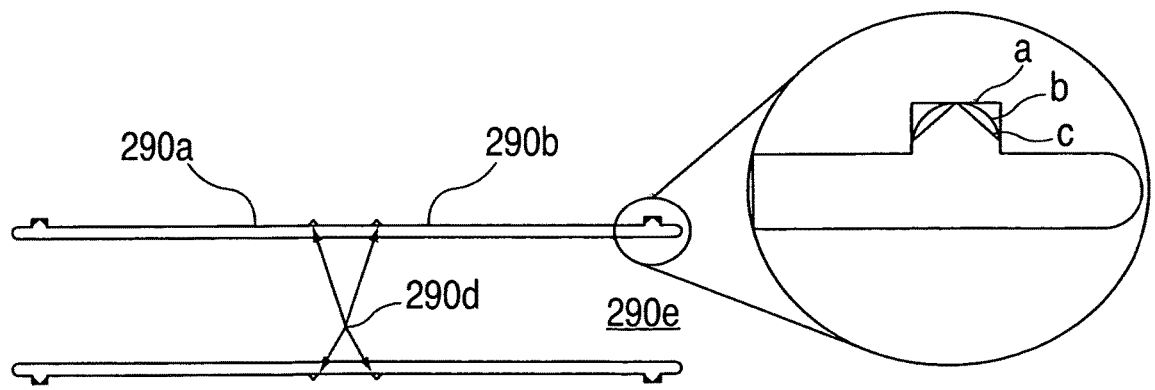

FIGS. 29A and 29B illustrate the use of focal elevating elements on a tack device of the type described above with respect to FIG. 25 having two or more concentric ring sections joined by bridges in between. FIG. 29A shows a cell of two adjacent ring sections 290a and 290b with strut sections 290c and which are joined in the middle by bridges 290d. FIG. 29B shows the ring sections expanded under expansion force and opposing sets of focal elevating elements 290e deployed on opposite ends of the two adjacent ring sections 290a and 290b. An inset to the figure shows the round elevating element having a height raised from the strut surface.

Figure 30A:
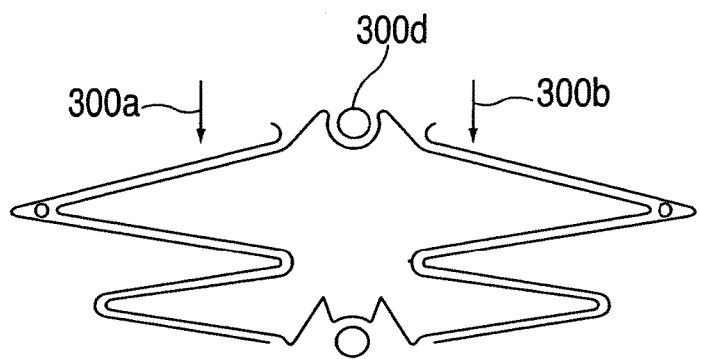
FIGS. 30A and 30B illustrate another variant of focal elevating elements on a tack device having two or more concentric ring sections.
Figure 30B:
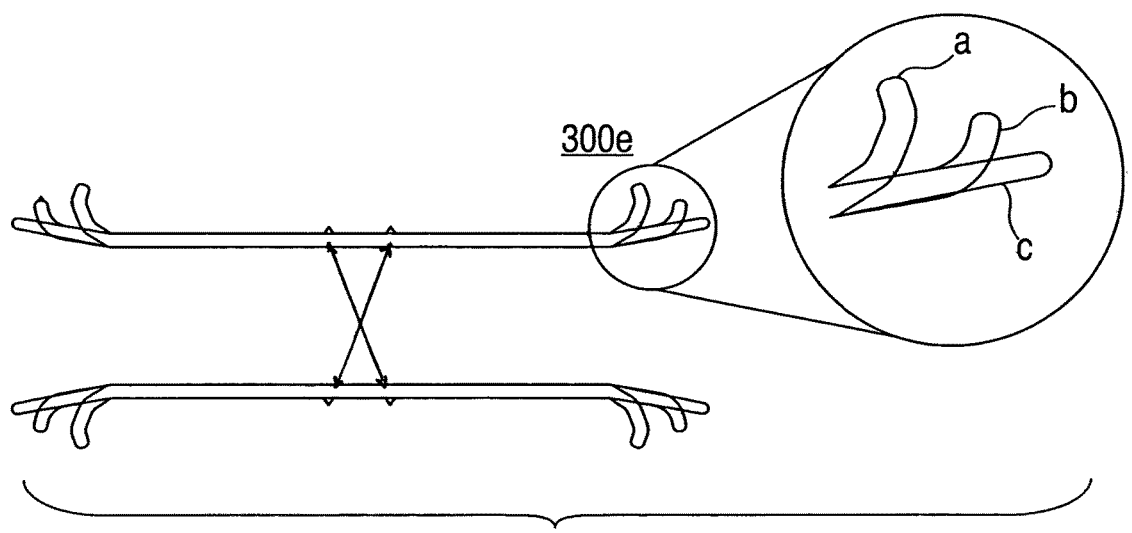

FIGS. 30A and 30B illustrate a cell of another variant of focal elevating elements formed on a tack device having two or more concentric ring sections 300a, 300b joined by bridges 300d in between. In this cell variant, the focal elevating elements 300e are formed by bending the sections of the strut (illustrated as the strut apex) out of the circumferential plane into varying degrees of tilt such as position "a", or position "b', up to a 90 degree vertical orientation shown in position "c" to form the elevating element.

Figure 31:
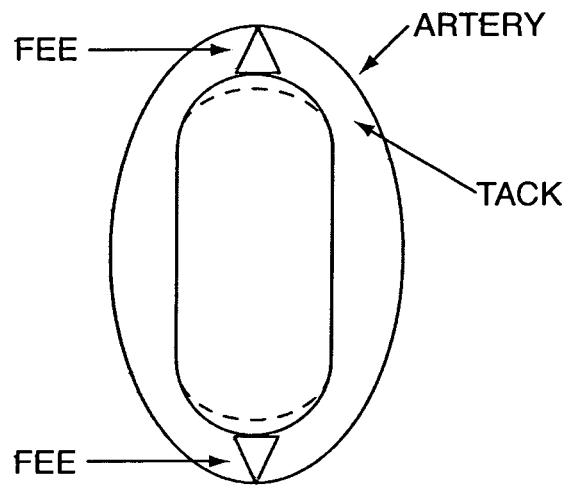
FIG. 31 illustrates the use of focal elevating elements to reshape artery walls into a desired cross-sectional shape.

Inherent in the use of shape memory alloys for the tack devices is the ability to conform to the shape of the blood vessel walls. Because the focal elevating elements can exert an expansion pressure on the blood vessel walls with a minimal risk of injury, they can be designed to reshape the blood vessel walls to a desired shape. FIG. 31 illustrates the focal elevating elements (FEE) positioned in diametrically opposite positions and formed with an extended height to reshape the artery walls into an ellipse cross-sectional shape which may better match the arterial cross section (such as an arterial branch) or expand the lumen to be more open in plaque-free areas.

Figure 32:
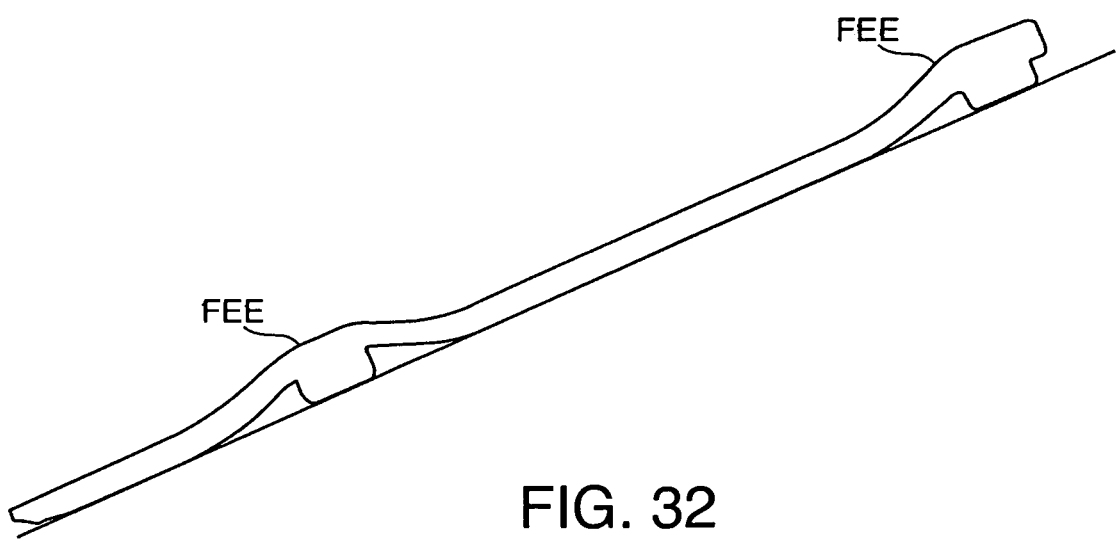

FIG. 32 shows a side view of FEEs spaced along a strut length having a small area lifted off the arterial due to the height of the FEE lifting a short distance of the neighboring strut length. Outward forces generated by the design or material used allow for only a small section on either side of the FEE to be lifted off the blood vessel wall.

Figure 33:
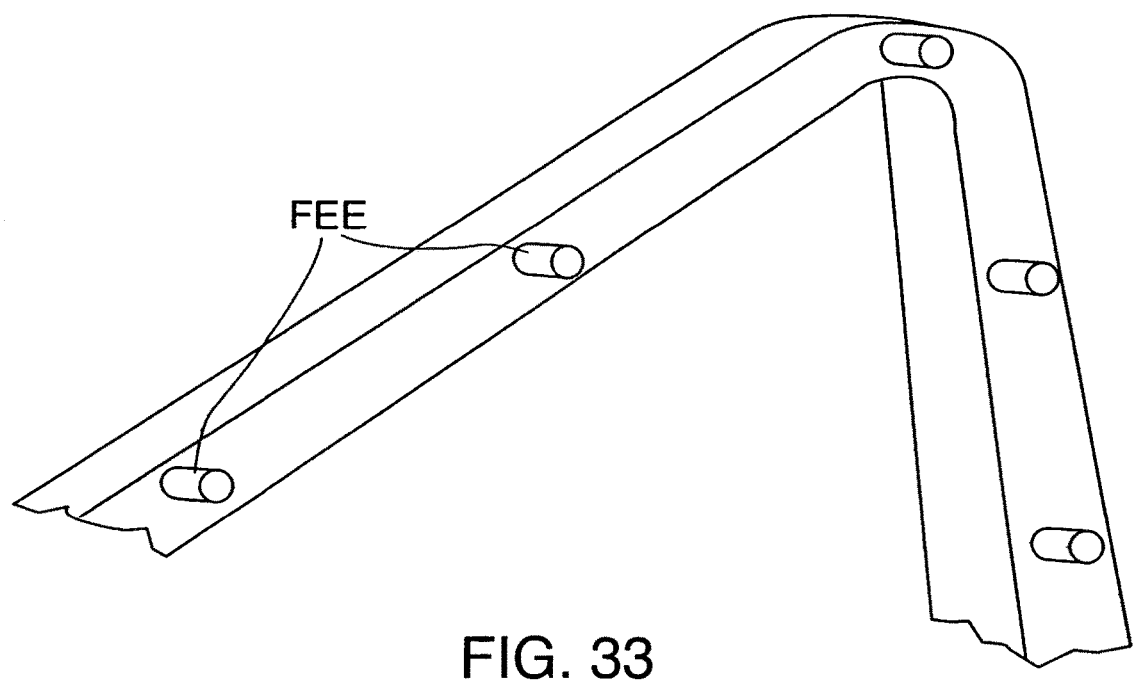

FIG. 33 illustrates a perspective view of a series of FEEs spaced along length of a strut section of a tack device.

Figure 34:
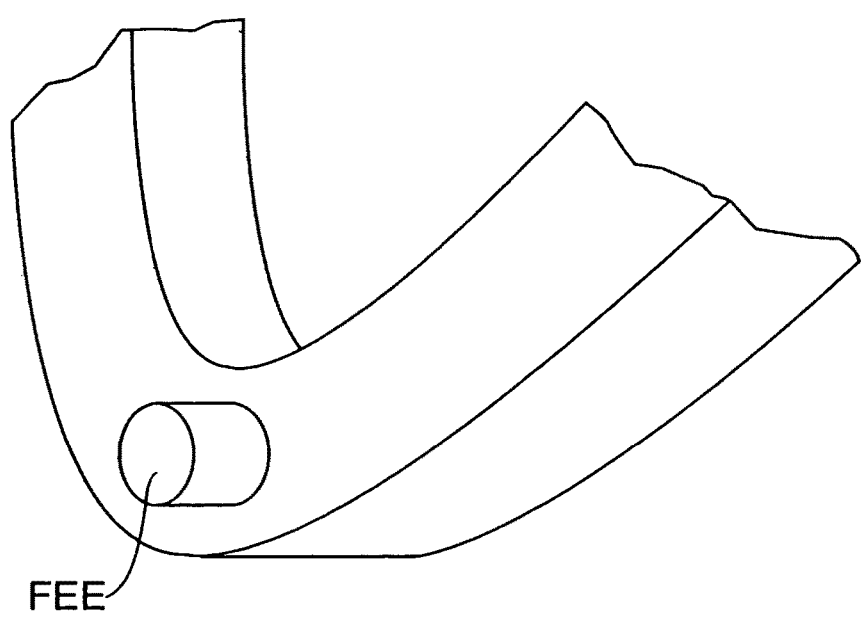

FIG. 34 illustrates a detailed view of a cylindrically shaped FEE placed at the apex of a strut section of the tack device.

Figure 35:
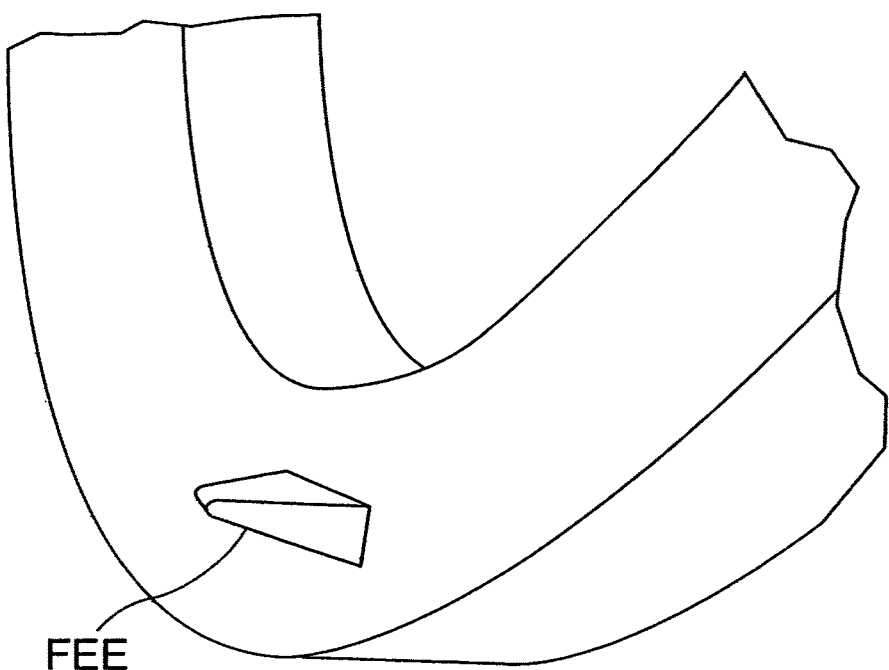

FIG. 35 illustrates a perspective view of a FEE formed as a pyramidical element at the apex of a strut section.

Figure 36:
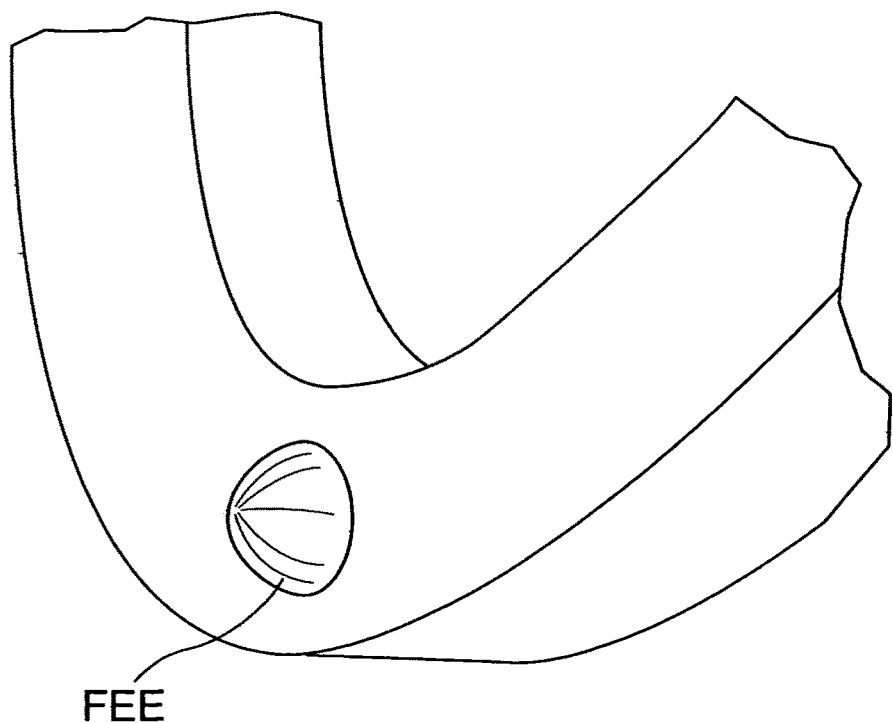

FIG. 36 illustrates a perspective view of a FEE formed as a dome element at the apex of a strut section.

Figure 37:
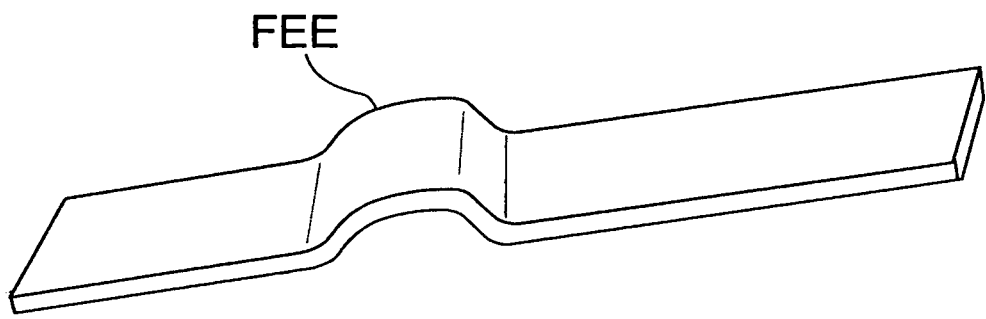

FIG. 37 illustrates a perspective view of a FEE formed by bending a portion of a strut length to raise it in height above the surface of the neighboring strut length.

Figure 38:
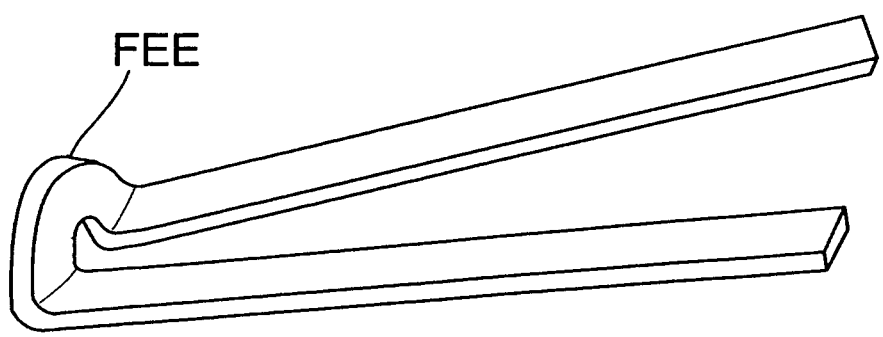

FIG. 38 illustrates a perspective view of a FEE formed by bending the apex of a strut section upward.

FIG. 39 illustrates a perspective view of a FEE formed by twisting a strut section (made from wire).

FIGS. 40A and 40B show a detailed view of the preferred embodiment of the plaque tack formed with concentric rings containing focal elevating elements at the apexes of the long struts and sets of barbs at the bridges.

In summary, the tack device of the present invention is used for plaque retention following balloon angioplasty treatment of atherosclerotic occlusive disease while avoiding problems with the use of stents due to installing a large mass of foreign material in the body which may cause injury, inflammation, and/or provide sites for restenosis. In contrast, the tack device minimizes the material structure and can be installed only at one or more plaque dissection sites that require retention. The improvement of using focal elevating elements on the tack periphery minimizes the contact surface area of the tack device with the blood vessel walls and reduces the risk of causing plaque dissection or injury to the blood vessel walls. This approach offers clinicians the ability to perform a minimally invasive post-angioplasty treatment and produce a stent-like result without using a stent.

It is to be understood that many modifications and variations may be devised given the above description of the principles of the invention. It is intended that all such modifications and variations be considered as within the spirit and scope of this invention, as defined in the following claims.

The invention claimed is:

1. An intravascular device comprising:
a frame consisting of only a single column of cells, the frame comprising:
a pair of concentric side rings comprising a single distal undulating ring and a single proximal undulating ring spaced apart coaxially from each other, each of said pair of concentric side rings having a compressed state and an expanded state and forming one end of the device; and
a plurality of longitudinally extending bridge members connecting the pair of concentric side rings, wherein each bridge member of the plurality of longitudinally extending bridge members connects to one of the pair of concentric side rings at one end and to the other of the pair of concentric side rings at an opposite end of the device; and
each of the bridge members comprising two pointed barbs extending from the bridge members in at least one of a circumferential manner and a tangential manner, wherein each of the two pointed barbs has a V-shape structure, and wherein a pointed end of the V-shape structure is pointed in a direction perpendicular to the longitudinal axis of the device;
wherein each cell of the single column of cells comprises a portion of each of the pair of concentric side rings and two of the plurality of longitudinally extending bridge members.

2. The device of claim 1, further comprising a plurality of focal elevating elements, each focal elevating element of the plurality located on an outer periphery of the device, each focal elevating element of the plurality located at a valley or peak on one of the pair of concentric side rings and having a pointed tip configured for contact with a tissue wall when implanted within a body.

3. The device of claim 1, wherein a diameter of each of said concentric side rings at the expanded state is about equal to a width of the device.

4. The device of claim 1, wherein each of the pair of concentric side rings is formed as a folding ring having a zigzag shape.

5. The device of claim 1, wherein the ratio of width of the concentric side ring to ring diameter is in the range of 1/10 to 1/100.

6. The device of claim 1, wherein the frame is made of a shape-memory alloy.

7. The device of claim 6, wherein the shape-memory alloy comprises Nitinol.

8. The device of claim 1, wherein the plurality of longitudinally extending bridge members comprise six or fewer bridge members between the two concentric side rings.

9. The device of claim 1, wherein the device is non-self-expanding and is configured to be applied with balloon expansion against plaque in a blood vessel.

10. The device of claim 1, wherein each of said pair of concentric side rings comprises a plurality of struts forming a dual amplitude ring.

11. A system comprising a delivery catheter and the intravascular device of claim 1 among a plurality of intravascular devices positioned on the delivery catheter.

12. The device of claim 1, wherein the frame is made of polyglycolic acid.

13. The device of claim 1, wherein the frame is made of a metal, a polymer, or a composite.

14. A system comprising:
a plurality of intravascular devices, each intravascular device consisting of:
a single frame consisting of a single column of cells, the frame comprising:
a pair of concentric side rings spaced apart coaxially from each other, each concentric side ring of said pair of concentric side rings comprising a plurality of struts forming a ring having a first amplitude and a second amplitude different from the first amplitude and, a compressed state and an expanded state, and forming one end of the intravascular device; and
a plurality of longitudinally extending bridge members connecting the pair of concentric side rings, wherein each bridge member of the plurality of longitudinally extending bridge members connects to one of the pair of concentric side rings at one end and to the other of the pair of concentric side rings at an opposite end of the intravascular device; and
each of the bridge members comprising two barbs extending from the bridge members in at least one of a circumferential manner and a tangential manner, wherein each of the two barbs has a V-shape structure, and wherein a pointed end of the V-shape structure is pointed in a direction perpendicular to the longitudinal axis of the device;
wherein each cell of the single column of cells comprises a portion of each of the pair of concentric side rings and two of the plurality of longitudinally extending bridge members.

15. The system of claim 14, further comprising a delivery catheter, wherein the plurality of intravascular devices are positioned on the delivery catheter in a compressed state.

16. The system of claim 14, wherein the frame is made of polyglycolic acid.

17. The system of claim 14, wherein the frame is made of a metal, a polymer, or a composite.

* * * * *